United States Patent
Jandali

(10) Patent No.: US 12,364,823 B2
(45) Date of Patent: Jul. 22, 2025

(54) SYSTEMS AND METHODS FOR BOTULINUM TOXIN OR OTHER DRUG INJECTIONS FOR MEDICAL TREATMENT

(71) Applicant: Mytox Ink, LLC, Southport, CT (US)

(72) Inventor: Shareef Jandali, Southport, CT (US)

(73) Assignee: MYTOX INK, LLC, Southport, CT (US)

(*) Notice: Subject to any disclaimer, the term of this patent is extended or adjusted under 35 U.S.C. 154(b) by 1133 days.

(21) Appl. No.: 16/792,130

(22) Filed: Feb. 14, 2020

(65) Prior Publication Data

US 2020/0179618 A1 Jun. 11, 2020

Related U.S. Application Data

(63) Continuation-in-part of application No. 16/570,515, filed on Sep. 13, 2019.

(Continued)

(51) Int. Cl.
*A61M 5/42* (2006.01)
*A61K 9/00* (2006.01)
(Continued)

(52) U.S. Cl.
CPC ........... *A61M 5/427* (2013.01); *A61K 9/0019* (2013.01); *A61K 38/164* (2013.01); *A61B 5/0077* (2013.01); *A61B 5/4839* (2013.01); *A61B 17/3403* (2013.01); *A61B 2017/3411* (2013.01); *A61K 38/4893* (2013.01); *A61M 5/158* (2013.01); *A61M 2205/583* (2013.01); *A61M 2207/00* (2013.01); *A61M 2209/088* (2013.01); *A61M 2210/0606* (2013.01); *G06T 17/00* (2013.01); *G06V 40/168* (2022.01)

(58) Field of Classification Search
CPC ..... A61M 5/427; A61M 5/158; A61K 9/0019; A61K 38/4893; G06T 17/00; G06V 40/168; A61B 17/3403; A61B 2017/3411
See application file for complete search history.

(56) References Cited

U.S. PATENT DOCUMENTS 9,199,044 B2 12/2015 Bangera et al.
9,205,204 B2 12/2015 Bangera et al.
(Continued)

FOREIGN PATENT DOCUMENTS

| CN | 10617625407/2016 | 7/2016 |
| CN | 10532669712/2017 | 12/2017 |
| EP | 296888201/2016 | 1/2016 |

OTHER PUBLICATIONS

International Search Report Written Opinion dated May 4, 2021, for International Application No. PCT/US21/16875 filed Feb. 5, 2021.
(Continued)

*Primary Examiner* — Nathan R Price
*Assistant Examiner* — Tania Ismail
(74) *Attorney, Agent, or Firm* — Neil D. Gershon

(57) ABSTRACT

A method for injection of drugs into a patient, the method including a) marking on a skin of the patient indicators to identify locations for drug injections: b) taking an image of the skin with the markings thereon; c) after obtaining a customized cover with openings in the cover, inserting a marking device through the openings to mark the skin for injection locations.

21 Claims, 34 Drawing Sheets

Related U.S. Application Data

(60) Provisional application No. 62/734,918, filed on Sep. 21, 2018.

(51) Int. Cl.
| | |
|---|---|
| *A61K 38/16* | (2006.01) |
| *A61B 5/00* | (2006.01) |
| *A61B 17/34* | (2006.01) |
| *A61K 38/48* | (2006.01) |
| *A61M 5/158* | (2006.01) |
| *G06T 17/00* | (2006.01) |
| *G06V 40/16* | (2022.01) |

(56) References Cited

U.S. PATENT DOCUMENTS

| | | |
|---|---|---|
| 9,551,882 B2 | 1/2017 | Read et al. |
| 9,629,963 B2 * | 4/2017 | Boyden ............. A61B 90/11 |
| 2004/0153031 A1 | 8/2004 | Van Kaauwen |
| 2005/0013850 A1 | 1/2005 | Caers et al. |
| 2005/0148935 A1 | 7/2005 | Dimitrova et al. |
| 2007/0255589 A1 | 11/2007 | Rodriguez |
| 2008/0058915 A1 | 3/2008 | Chang |
| 2010/0198153 A1 | 8/2010 | Yang |
| 2014/0039658 A1 | 2/2014 | Bangera et al. |
| 2014/0261430 A1 | 9/2014 | Davis |
| 2015/0366327 A1 | 12/2015 | LaHood, Sr. et al. |
| 2016/0088920 A1 | 3/2016 | LaHood, Sr. et al. |
| 2016/0242853 A1 | 8/2016 | Bangera et al. |
| 2017/0252108 A1 | 9/2017 | Rios et al. |
| 2017/0293286 A1 | 10/2017 | Aggarwal et al. |
| 2019/0365495 A1 | 12/2019 | Heath et al. |
| 2020/0093997 A1 | 3/2020 | Jandali et al. |

OTHER PUBLICATIONS

International Search Report Written Opinion dated Jan. 24, 2020 for International Application No. PCT/US19/51068 filed Sep. 13, 2019.

* cited by examiner

```
                          ┌─ Directly through pre-formed holes
Injection of Botulinum toxin ─┼─ Through pre-loaded syringes
through mask of patient       └─ Through replaceable syringes
```

FIG 3

```
         ┌─ Take Photos ─┐
Patient ─┼─ Answer questions ─┤ Software → 3D Representation
         └─ Upload photos ─┘                Injection Locations
                                                    │
                                                    ↓
Physician ─────────────────────────────── Custom mask printed
```

FIG 4

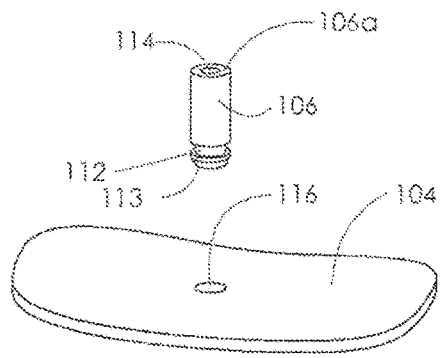
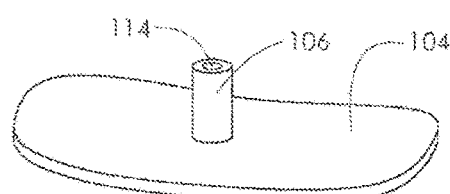
FIG. 17
FIG. 18
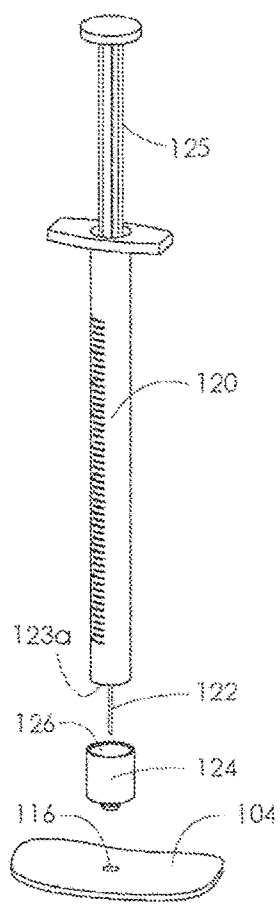
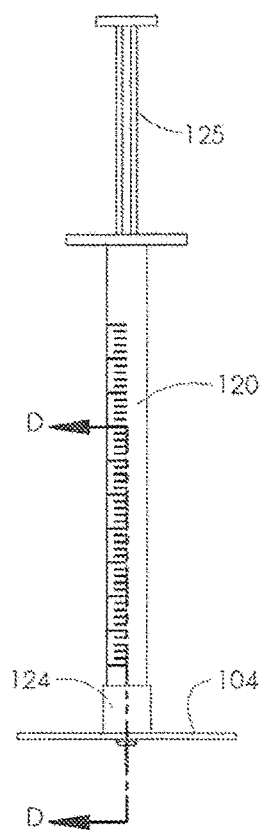
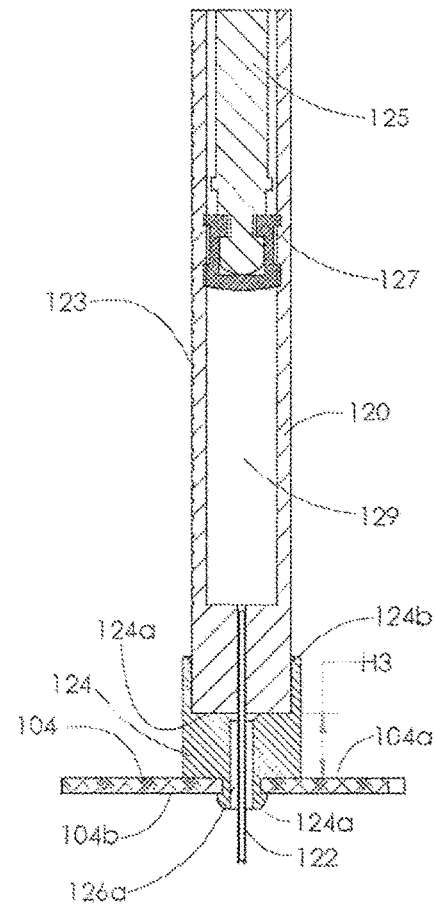
FIG. 19
FIG. 20
FIG. 21

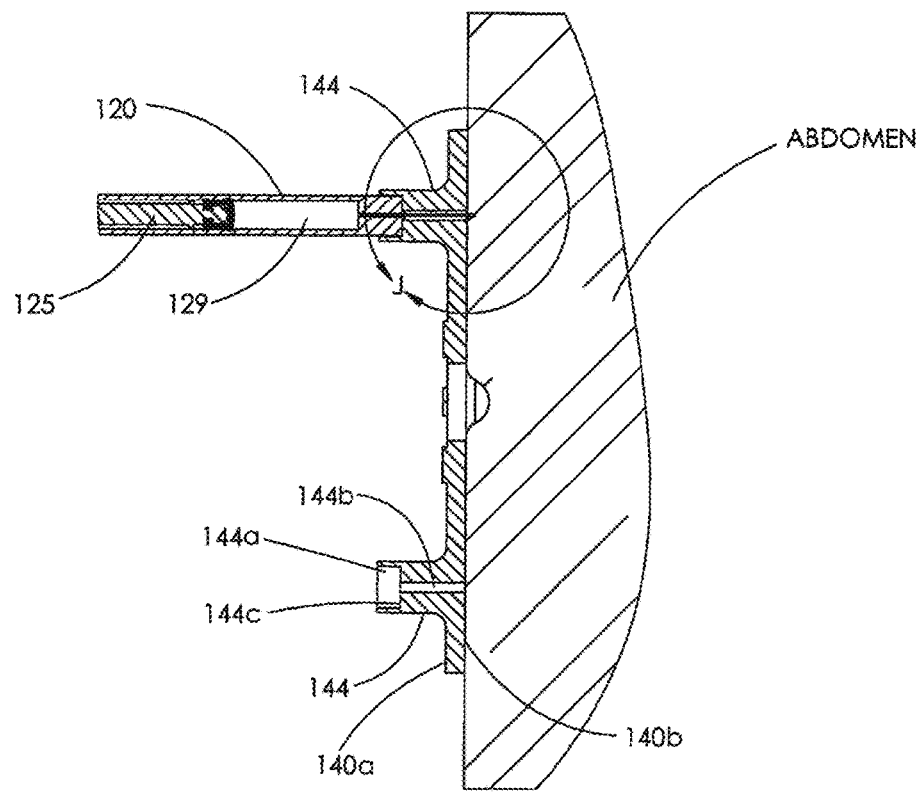
FIG. 32
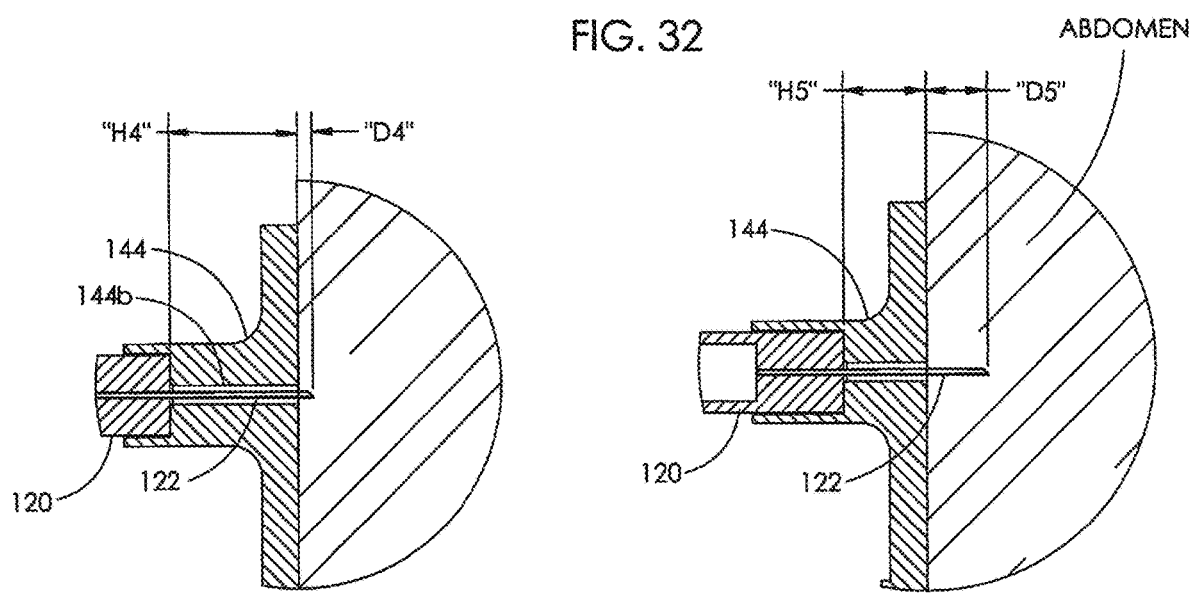
FIG. 33
FIG. 34

SYSTEMS AND METHODS FOR BOTULINUM TOXIN OR OTHER DRUG INJECTIONS FOR MEDICAL TREATMENT

This application is a continuation in part of application Ser. No. 16/570,515, filed Sep. 13, 2019, which claims priority from provisional application Ser. No. 62/734,918, filed Sep. 21, 2018. The entire contents of each of these applications are incorporated herein by reference.

BACKGROUND

Technical Field

This application relates to systems and methods for drug injections, and more particularly, to customized patient masks, and processes for forming the masks, for facilitating injections of drugs such as botulinum toxin.

Background of Related Art

Botulinum toxin is a neurotoxin made from a toxin produced by the bacterium *Clostridium botulinum*. Doctors use this drug in small doses in cosmetics for temporary smoothing of facial wrinkles and improving appearance. The injections work by weakening or paralyzing certain muscles or by blocking certain nerves. The effects last about three to twelve months, depending on what is being treated. There are various types of botulinum toxin, marketed under brand names such as Botox (onabotulinumtoxinA, Allergan) and Dysport/Azzalure (abobotulinumtoxinA, Ipsen/Galderma), Xeomin/Bocouture (incobotulinumtoxinA, Merz) and Jeuveau (prabotulinumtoxinA, Evolus/Daewoong), along with several others in clinical trials.

Botulinum toxin is typically injected in the human face. The effects of current botulinum toxin injections for glabellar lines (lines between the eyes) typically last two to four months, although this is patient, and in some cases, product-dependent, with some patients experiencing a longer duration of effect. Injection of botulinum toxin into the muscles under facial wrinkles causes relaxation of those muscles, resulting in the smoothing of the overlying skin. Smoothing of wrinkles is usually visible three-five days after injection, with maximum effect typically a week following injection. Muscles can be treated repeatedly to maintain the smoothed appearance.

Patients frequently complain about how their botulinum toxin (e.g., Botox, Dysport, Xeomin) injections for wrinkles/frown lines differ due to variability in where it is injected at various practitioner's offices or even in some cases in the same office by the same practitioner. This variability, for example, can change the shape of one's eyebrows, making them too arched, too flat, drooping, etc., or not provide the desired wrinkle reduction. This variability also results in a different appearance than the patient might have expected. The variability in the patient anatomy and muscles under the skin is the reason there is variability in patient results with injections.

The need exists for achieving more consistent results for botulinum toxin injections. The need further exists for botulinum injections which better conform to the individual patient's objectives. Such systems which deliver more consistent results and better conformance to desires would beneficially also have use in other surgical applications/procedures. Such systems would also be beneficial if they could improve results while also improving convenience and reducing costs to the patient.

SUMMARY OF THE INVENTION

The present invention advantageously overcomes the problems and deficiencies of the prior art. The present invention provides various systems and methods to achieve more consistent results from botulinum toxin injections (or from other drug injections). The present invention also provides various systems and methods that are more responsive to the patient's wishes. These systems and methods provide for input of the anatomical structure of the patient's face and/or scalp (or other body regions), input of location for injections, and/or creation of 3D masks with injection locators in response to the input. In alternate embodiments of the present invention, the 3D masks are created with openings for markers so that the physician can mark the patient's skin to provide consistent injection locations. Each of these systems and methods are discussed in detail below.

The present invention provides customized masks that can in their simplest forms provide locators for fluid injections by the physician. The present invention in alternate embodiments can provide customized masks with locators for attachable injection devices or with integral injection devices. The present invention in alternate embodiments provides customized masks with locators for skin markings on the patient. These various embodiments are discussed in detail below.

The present invention also provides in some embodiments systems and methods that enable the patient rather than the doctor to inject the fluid, as discussed in detail below.

In accordance with one aspect of the present invention, a method for creating a customized cover (mask) for injection of drugs into a patient is provided, the method comprising a) marking on a skin of a patient indicators to identify locations for drug injections: b) taking an image of the skin with the markings; and c) inputting the image to create a cover with openings corresponding to the markings on the skin, the openings extending through the cover dimensioned for insertion of markers through the cover to enable repeated markings through the cover.

In accordance with another aspect of the present invention, a method for creating a customized cover for injection of drugs into a patient is provided based on utilization of a customized cover formed by data input of anatomical features of a patient, the method comprising a) marking on a skin of a patient indicators to identify locations for drug injections; b) taking an image of the skin with the markings thereon to provide data input for the cover; and c) after obtaining a customized cover with openings in the cover, inserting a marking device through at least one of the openings to mark the skin for injection locations.

In accordance with some embodiments, the method further comprises the step of marking the skin with varied color markings to indicate a different dosage of the drug for injection.

In some embodiments, the method further comprises the step of removing the cover after the markings are made through the openings with one or more marking devices and injecting the drug at the locations of markings.

In some embodiments, the cover has designations integrally formed thereon, or alternatively applied to the cover after the cover is formed, to indicate dosage, and the method further comprises removing the cover and injecting the drug into the patient in accordance with the indicated dosage.

In some embodiments, the method further comprises the step of aligning the cover on the skin in accordance with at least one alignment marker on the cover.

In some embodiments, the method further comprises the step of editing the image to provide a revised image and uploading the revised image to provide a guide for forming the cover.

In accordance with another aspect of the present invention, a method for providing consistent injection of a drugs through a skin of a patient is provided, the method comprising the steps of:

a) manually providing first markings on the skin of a patient to provide locators for drug injection;

b) taking a first image of the skin with the first markings thereon;

c) storing the first image;

d) injecting a drug into the patient at the location of the first markings;

e) after a period of time, evaluating the result of the injection of the drug and either i) editing the first image to adjust one or more injection locations or ii) not editing the first image;

f) after obtaining a cover made in accordance with either the edited or not edited first image, placing the cover on the skin and manually providing second markings through openings in the cover; and g) removing the cover and injecting the drug at the second markings.

In some embodiments, the method further comprises the step of uploading either the edited or unedited first image to a web portal for linking with a device for manufacturing the cover.

In accordance with another aspect of the present invention, a customized cover for placement over a portion of a body of a patient is provided, the cover having a plurality of openings extending therethrough configured and dimensioned for manual insertion of markers by a health care provider to provide marked locations on the patient for injection of one or more drugs. The cover is manufactured from a set of instructions produced from a software based application processing an image of an anatomical view of the patient with markings thereon. The cover is customized to the portion of the body based on the software based application and the plurality of openings are customized to the desired locations of markings through the cover for subsequent injection of one or more drugs independent of the cover.

In some embodiments, the cover is configured for placement over a face of a patient. In some embodiments, the cover includes one or more alignment markings to align the cover on the body. In some embodiments, the cover includes dosage indicators thereon.

In some embodiments, the image is inputted (uploaded) to a website portal linked to a software application on a device which receives and processes data corresponding to desired locations of drug injection based on the manually marked locations to provide the set of instructions for manufacture of the cover. In some embodiments, the image is manipulated prior to input to a website portal; in other embodiments the image is uploaded to the website portal and then manipulated.

In some embodiments, the customized cover is formed by 3D printing.

In some embodiments, the cover is manufactured based on human editing on the software program.

In accordance with another aspect of the present invention, a method for making a customized cover for placement over a portion of a body of a patient is provided. The cover is made with a plurality of openings extending therethrough configured and dimensioned for manual insertion of markers by a health care provider to provide marked locations on the patient for injection of one or more drugs. The cover is made based on input of a set of instructions produced from a software based application processing an image of an anatomical view of the patient with markings thereon. The cover is made customized to the portion of the body based on the software based application and the plurality of openings are made customized to the desired locations of markings through the cover for subsequent injection of one or more drugs independent of the cover.

In accordance with another aspect of the present invention, a cover (mask) for placement over a portion of a body of a patient is provided. The cover has a plurality of openings extending therethrough for injection of a drug into the body, the cover being customized to the portion of the body and the plurality of openings being customized to the desired locations of injection of the drug through the openings and into the body.

The openings in some embodiments are configured for passage of an injection needle through the cover and into the body. The cover can be configured for placement over a face of a patient, an abdomen of the patient, or other body regions such as the chest, arms legs or back.

In some embodiments, a plurality of injection devices are attached to the cover, each of the injection devices communicating with one of the plurality of openings for injection of the drug through the openings. The injection devices can in some embodiments be provided pre-filled with the drug.

In some embodiments, the cover includes a plurality of guides extending proximally from the cover having a lumen to receive at least a portion of an injection device, and the guides communicate with respective openings of the cover. In some embodiments, the guides are removably attachable to the cover; in other embodiments, the guides are integral with the cover.

In accordance with another aspect of the present invention, a cover for placement over a portion of a body of a patient is provided. The cover has a plurality of openings for injection of a drug into the body, the cover being customized to the portion of the body. The cover has a plurality of guides extending proximally from the cover in alignment with the openings, the guides having a lumen configured to receive at least a portion of an injection device for injection of the drug.

In some embodiments, the guides are removably attachable to the cover; in other embodiments, the guides are integral with the cover. The cover can in some embodiments, include one or more alignment markings to align the cover on the body.

In accordance with another aspect of the present invention, a system for drug injection into an anatomical region of a patient is provided. The system includes an input subsystem to provide data on the region of the patient and an output subsystem to provide a customized cover for the region of the patient, the customized cover having openings to enable passage of the drug through the cover into the region of the patient.

In some embodiments, the input subsystem includes images of the region of the patient. The images can be digital photos, created by a 3D scanner or by other methods.

In some embodiments, the input subsystem includes an app for receiving and processing data corresponding to desired locations of drug injection by the patient. In some embodiments, the output subsystem includes a 3D printing of the customized cover with the openings pre-formed in the cover. In some embodiments, the input subsystem includes markings placed on the images or, alternatively, markings placed on the region prior to imaging, to provide opening (injection) locators.

The system can include a plurality of injection devices removably mountable to the cover for injection of the drug into the region of the patient.

In accordance with another aspect of the present invention, a system for drug injection into an anatomical region of a patient is provided. The system includes an input subsystem to provide data on the region of the patient and an output subsystem to provide a customized cover for the region of the patient, the customized cover having openings to enable passage of markers through the cover into the region of the patient.

In accordance with another aspect of the present invention, a kit for injecting a drug into a patient is provided comprising a) a cover for placement over a portion of a human body, the cover having a plurality of openings for injection of a drug into the body, the cover being customized to the patient; and b) a plurality of injection devices for connection to the cover to inject the drug through the openings in the cover.

In some embodiments, the injection devices are pre-filled with the drug.

In accordance with another aspect of the present invention, a method for creating a customized cover to provide location regions for injection of drugs into a patient is provided, the method comprising the steps of:
  a) processing images of a region of the patient;
  b) identifying locations for openings in the cover based on the images to identify locations for drug injection; and
  c) creating the customized cover with the openings.

In some embodiments, the method further comprises the step of taking images of the region of the body for processing of the images.

In some embodiments, the method further comprises the step of receiving images of the region of the body obtained by an outside source, the receiving step occurring before the step of processing the images. In some embodiments, the images are taken via a digital camera; in other embodiments, the images are taken via a scanner.

In some embodiments, the step of creating the cover comprises the steps of providing a 3D image for processing for performing step (a) above and 3D printing the customized cover. In some embodiments, the method includes the step of shipping the cover to a doctor's office; in other embodiments, the method includes the step of shipping the cover directly to the patient.

In accordance with another aspect of the present invention, a method for creating a customized cover for injection of drugs into a patient is provided, the method comprising a) identifying locations for openings on a 3D image to identify locations for pre-formed openings in the cover for drug injection; and b) creating the cover with the openings. The method can in some embodiments include the step of creating the cover with a plurality of guides for receiving injection devices for injection of the drugs.

In accordance with another aspect of the present invention, a method for creating input for a customized cover for injection of drugs into a patient is provided, the method comprising a) identifying locations for openings to identify locations for pre-formed openings in the cover for drug injection; and b) storing a 3D image with the identified locations.

In some embodiments, the step of identifying locations for openings comprises marking the locations directly on the body region of the patient. In other embodiments, the step of identifying locations for openings comprises marking the locations on a 3D image of the body region of the patient.

The method can further include the step of transferring the stored data to a system for creating the customized mask. In some embodiments, the system is a 3D printer. In some embodiments, the method includes the step of taking digital photos to create the 3D image.

In accordance with another aspect of the present invention, a method for creating input for injection of drugs into body region of a patient is provided comprising a) identifying body region locations to identify locations for drug injection; b) storing a 3D image with the identified locations; and c) projecting the image onto the body region. In some embodiments, the image is projected from a mobile device.

In accordance with another aspect of the present invention, a method for creating a customized cover for injection of drugs into a patient is provided, the method comprising a) marking on a skin of a patient indicators to identify locations for drug injections: b) taking an image of the skin with the markings; and c) utilizing the image to create a cover with openings corresponding to the markings on the skin, the openings extending through the cover to enable drug injection through the cover.

In some embodiments, the method includes the step of providing a coded designation adjacent the openings to indicate the desired dosage of the drug injection through the openings. In some embodiments, the coded designation is integral with the cover. In other embodiments, the coded designation is applied to the cover after the cover is formed.

In accordance with another aspect of the present invention, a method of creating a customized cover for drug injection is provided, the method comprising the steps of
  e) receiving, by an apparatus, input from a patient regarding cosmetic parameters;
  f) identifying, by the apparatus, in response to receiving the input, locations for openings for the customized cover; and
  g) storing, by the apparatus, the identified locations on a 3D image contained by the apparatus.

In some embodiments, the method includes the step of creating a 3D model from the stored image of step (c). The method can include printing via a 3D printer the cover from the 3D model. In some embodiments, the step of receiving input includes responses to questions regarding appearance objectives of the patient.

BRIEF DESCRIPTION OF THE DRAWINGS

Preferred embodiment(s) of the present invention are described herein with reference to the drawings wherein:

FIG. 2I is a flow chart depicting an alternate system of the present invention;

FIG. 3 is a block diagram illustrating the alternate injection methods of the customized mask of the present invention;

FIG. 4 is a block diagram illustrating the system of the embodiment of FIG. 1A;

FIG. 17 is a close up perspective view of the guide channel of FIG. 12B prior to insertion into the mask;

FIG. 18 is a close up perspective view of the guide channel of FIG. 12B attached to the mask;

FIG. 19 is a perspective view showing a syringe and a needle guide channel in accordance with an alternate embodiment of the present invention;

FIG. 20 is a front view showing the syringe inserted into the guide channel of FIG. 19;

FIG. 32 is a cross-sectional view taken along line G-G of FIG. 29;

FIG. 33 is close up view of the area of detail J of FIG. 32;

FIG. 34 is a view similar to FIG. 33 showing an alternate embodiment of the syringe guide channel having a shorter height to increase the depth of needle insertion;

DESCRIPTION OF PREFERRED EMBODIMENTS

Figure 1A:
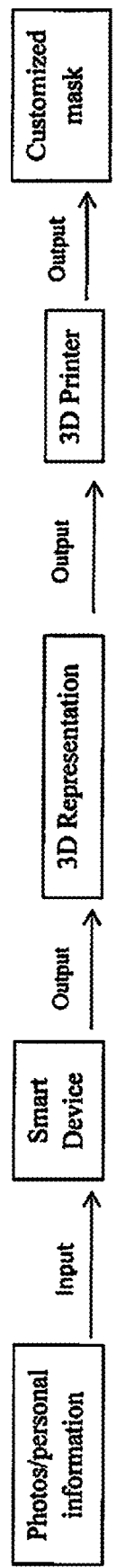
FIG. 1A is a diagram of the overall system in accordance with one embodiment of the present invention.

The present invention provides patient masks with preformed holes, and processes for making such masks, for injection of botulinum toxin, or in alternate embodiments, other drugs or medicines. In some embodiments, the masks are formed to provide openings for insertion of markers to mark injection locations on the skin; in other embodiments, the masks are formed to provide openings for insertion of injection needles. In some embodiments, the masks are printed in a doctor's office or in a health clinic and provided to the patient's doctor; in other embodiments, the masks are printed at a central location and sent to the doctor or provided directly to the patient who can bring the mask to the doctor. In still other embodiments, the masks are printed at a central location and sent along with pre-filled syringes directly to the patient. In this latter embodiment, the patient is injecting the drug without the need for a physician; in the former embodiments, the patient relies on the physician to inject the drug. Each of these embodiments is discussed in detail below. Note the masks are also referred to herein as "covers" as they cover a portion of the patient's body, and are thus not limited to covering the patient's face or forehead. Thus, the term "mask" and "cover" are used interchangeably herein. The customized mask (cover) forms the output subsystem of the overall system of the present invention.

Note that injection by a physician as used herein is meant to differentiate from injection by a patient. It should be appreciated that injection by a physician (also considered a "health care provider") includes an injection by another health care provider, such as a nurse, physician assistant, pharmacist, etc. (and not by the patients themselves).

Various imaging devices can be utilized for the foundation for the custom masks. Examples of such imaging devices are described below.

In the embodiments described below, the locations for injections can be provided by physician input, e.g., the physician marking the particular locations of the patient's face or forehead or marking the locations on a 3D image. In alternate embodiments, the software algorithm of the app determines the injection locations based on patient input in the app. In either case, the mask is created customized to the patient's anatomy and goals. These various inputs form input subsystems of the system of the present invention to provide data on the anatomical region of the patient and desired injection locations.

The masks can be of various shapes and configurations. Several examples are shown in the illustrated drawings. The masks can be created by various methods and in some embodiments are provided with openings at the desired locations for injection. In some embodiments, the masks can also be created with indicators of the recommended dosage at each of the injection sites (openings). The syringes for injections through the masks can be provided separate from or alternatively in conjunction with the mask, each of these versions discussed below. In short, the customized masks of the present invention essentially provide a roadmap for drug or medicine injection to facilitate injection and provide more consistent injections to provide more consistent and improved results. The reuse of the mask on the patient provides a continuous roadmap for the multiple injections typically spaced over a determined time period. For reuse on the patient, the mask can be wiped down with for example an alcohol pad or an antiseptic wipe.

Note as used herein, the syringe forms one type of injection device, it being understood that other types of injection devices can be utilized to inject the drug.

Figure 1B:
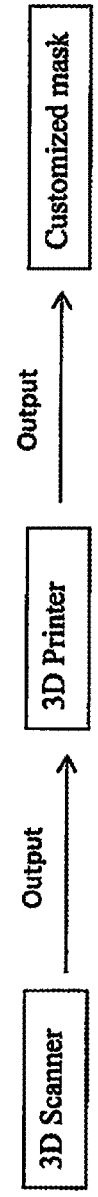
FIG. 1B is a diagram of the overall system in accordance with an alternate embodiment of the present invention.
Figure 2A:
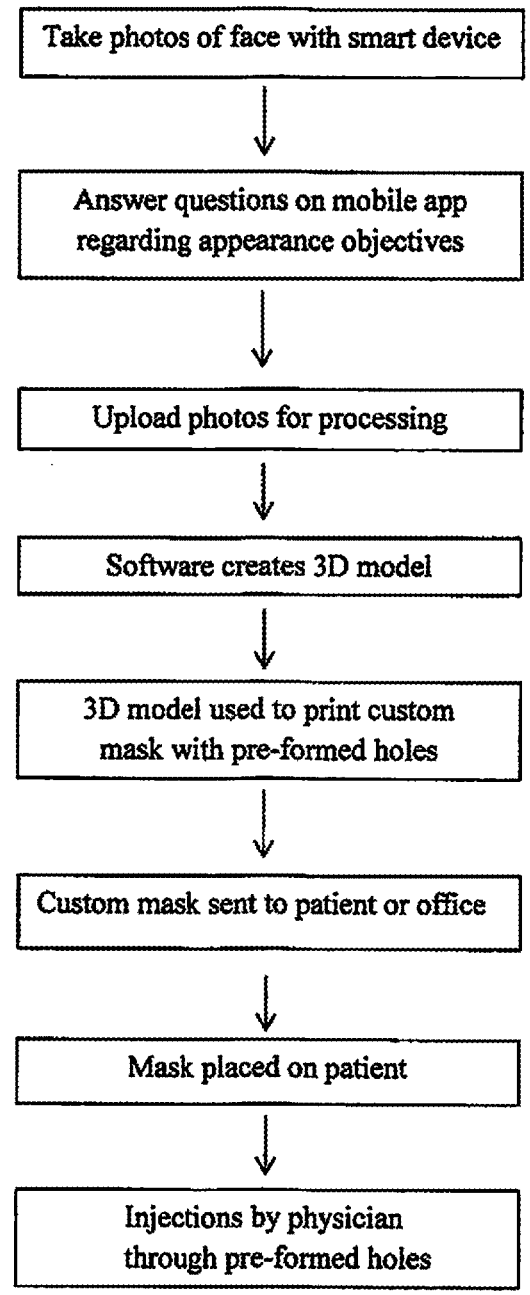
FIG. 2A is a flow chart depicting in more detail the steps of the system of FIG. 1A.
Figure 2B:
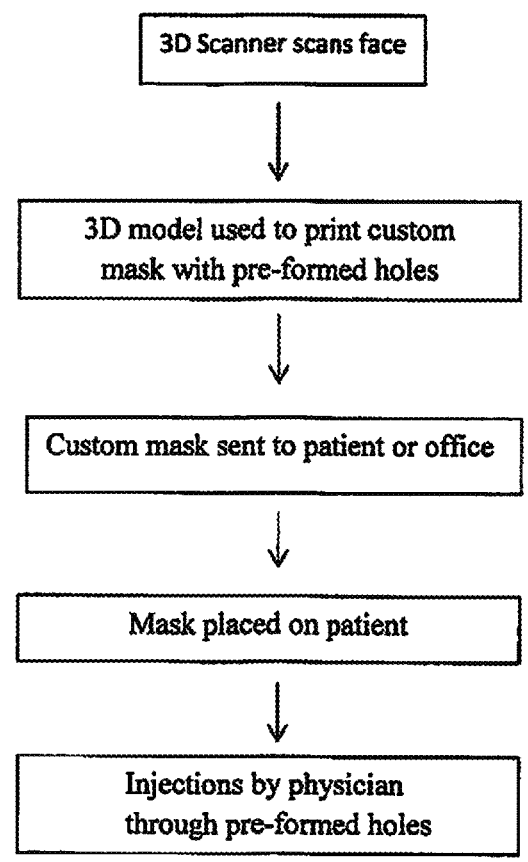
FIG. 2B is a flow chart depicting in more detail the steps of the system of FIG. 1B.

Referring now to the drawings wherein like reference numerals identify similar structural features of the apparatus disclosed herein, FIGS. 1A and 2A illustrate one embodiment of the system/method process of the present invention and FIGS. 1B and 2B illustrate an alternate embodiment of the system/method process of the present invention. The methods differ in how the data is collected for formation of the customized masks of the present invention, however, in both systems, the face/scalp mask is created with pre-formed holes to satisfy the needs of the individual patient and enable predictable and consistent cosmetic results of the treatment. Note the discussion of FIGS. 1A-48 herein is, for convenience, discussed in terms of botulinum toxin for cosmetic treatment; however, it should be understood that the same systems and methods/processes can be utilized for injections of other fluids, e.g. drugs or medicines, such as Kybella (deoxycholic acid) by way of example. Thus, the present invention is not limited to botulinum injection. Also, the masks (covers) discussed below which are placed over the patient's face or forehead for injection locators or for marker locators are discussed for such use to provide one example of a cover for the patient for injections, it being understood that the covers for injection locators or for marker locators can alternatively be placed in other regions of the body, such as over the abdomen as shown in FIGS. 25-34 by way of example, or in other body regions such as the chest, arms legs or back. It should also be understood, that the injection devices and guide channels discussed herein can be used with any of the covers disclosed herein, or with alternative embodiments of the covers.

Note as used herein the term "distal" denotes components, regions or sections closer to the patient's body and the term "proximal" denotes components, regions or sections further from the patient's body.

Turning initially to FIG. 1A, a block diagram of the system of a first embodiment of the present invention is illustrated. In this embodiment, the patient takes photos/pictures and then enters personal information into the smart device, e.g., IPhone, IPad, tablet etc. which includes the patient's objectives and desired results from the treatment as directed in the app. These inputted photos and information regarding cosmetic parameters are then analyzed and processed by the app algorithms (or in alternate embodiments by a physician, provider, or technician at a company remote site) which is then used to create a three dimensional (3D) representation on the smart device, stored for transmission and printing.

In the next step, the 3D representation is transmitted to a 3D printer which prints a customized mask or mold for the patient in accordance with the 3D representation. The customized mask is printed with openings, responsive to the patient input on the app, for fluid injection (or for markers) as described in more detail below. The fluid injection can be performed in various ways such as depicted in FIG. 3 discussed below.

More detailed steps of the system and method of FIG. 1A are depicted in the flow chart of FIG. 2A which shows the process start to finish. In the first step, the patient, with a smart device, takes a photo or series of photos of his/her face and/or scalp and/or other body region, depending on the desired location for botulinum injections. In the next step, the patient answers a series of questions on an app as to what the patient desires with regard to the botulinum toxin injections, e.g., wrinkles, eyebrows lifted, natural appearance, etc. In the following steps, the photos are uploaded for processing and software on the smart device (or in alternate embodiments a central server at a company remote site) converts them to a 3D model. The 3D model, in the next step, is then inputted to a 3D printer which prints out a custom mask for the patient's face and/or scalp (or other body region) which has pre-formed holes/openings to guide injections, the holes created in response to the input on the app regarding the injections. In some embodiments, the software algorithm identifies the location of the holes in response to the patient's input regarding the desired treatment results. In other embodiments, the physician or technician utilizes the patient's input to map out the location of the injection holes on the program. In either case, the customized mask is created by the 3D printer and can be sent directly to the patient who can bring it to a physician's office, or alternatively, the mask can be sent directly to the physician/practitioner's office. In some versions, the physician office or health clinic can be equipped with the 3D printer so the masks can be printed at the office or clinic. In any of these arrangements, when treatment is scheduled, the mask is placed on the patient and then injections of the botulinum toxin are made by the physician in the pre-formed holes in the mask in accordance with the last step on the flow chart of FIG. 2A. This system improves the predictability/consistency of treatment. Note the injections can be in accordance with the variations of FIG. 3 discussed below. Various features on the mask can aid injection as discussed in detail below.

The injections through the mask can be effected in several ways, as depicted in the diagram of FIG. 3: 1) directly through the pre-formed holes (openings) in the mask wherein the physician utilizes fluid injection devices inserted through the holes; 2) via pre-loaded syringes extending into the mask which can be mounted to the mask (see e.g., FIG. 7); and/or 3) via replaceable syringes which are mounted on the mask. These last two methods provide a more automated system. The pre-formed holes not only provide locators for injections but also inform the physician of the number of units to inject. Depth control of injections can be provided by the mask as discussed below. Various masks are illustrated in the drawings and are discussed in more detail below.

Figure 2C:
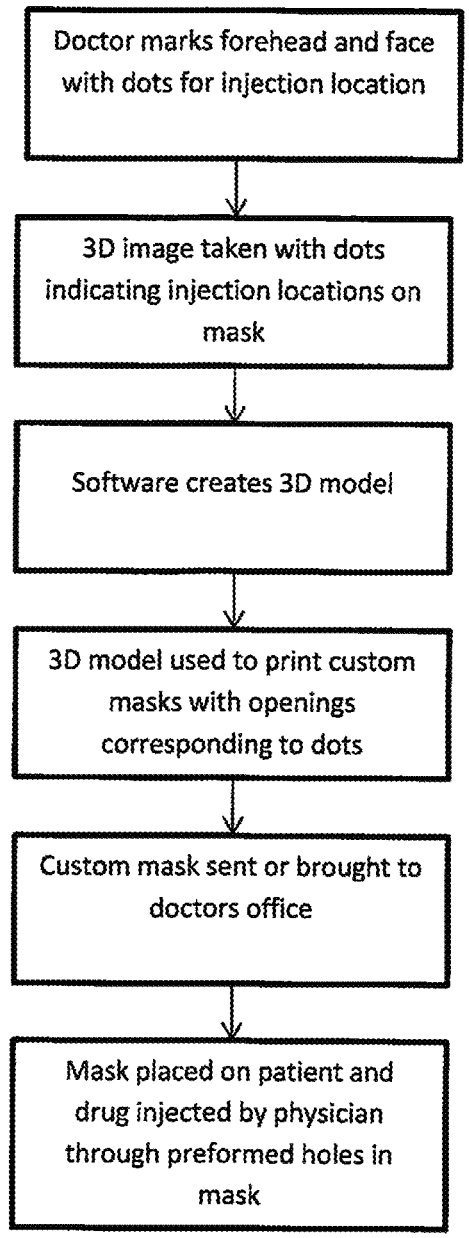
FIG. 2C is a flow chart depicting an alternate system of the present invention for use by a physician.
Figure 2D:
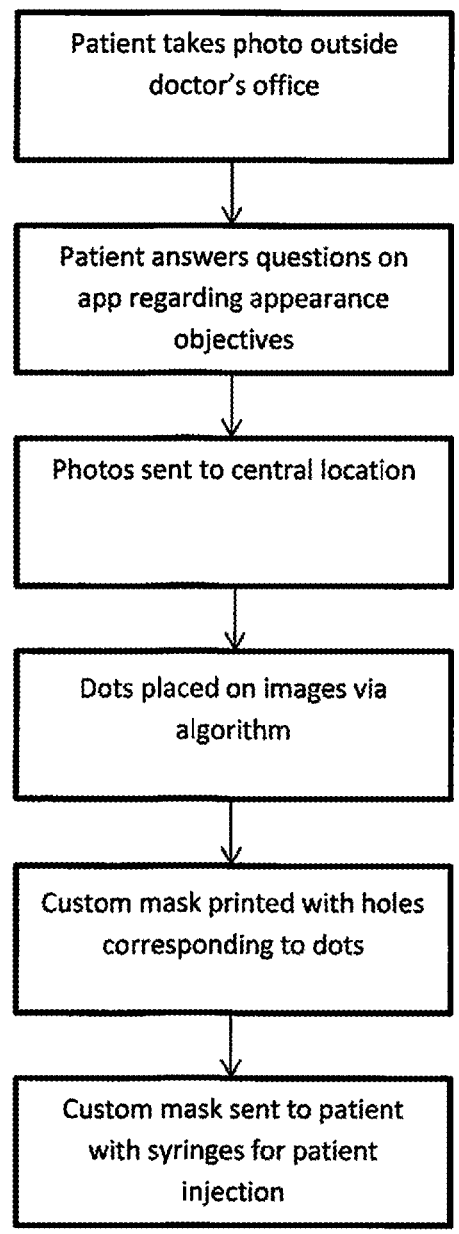
FIG. 2D is a flow chart depicting an alternate system of the present invention for use by a patient without the role of the physician.
Figure 2E:
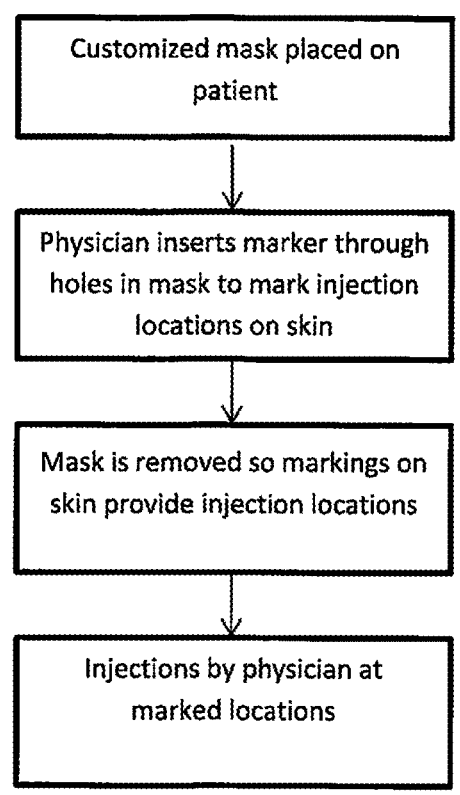
FIG. 2E is a flow chart depicting an alternate system of the present invention.
Figure 2F:
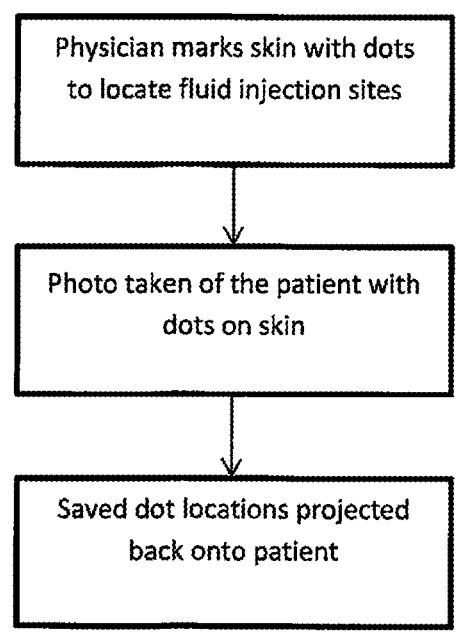
FIG. 2F is a flow chart depicting an alternate system of the present invention.

In an alternate embodiment, depicted in the flow chart of FIG. 2E, a projected image/hologram is used instead of a 3D printed mask. In this method/system, the physician marks the face (or other body region) of the patient with spots (dots) for fluid injection, e.g. Botox injection. A photo of the face is taken with a mobile device or camera. The saved dot locations are then projected back onto the patient's face through a free-standing projector or a projector out of a mobile device. The image with the dot locations and color/unit dosages are then projected back onto the person's face (like a hologram) the next time they get their injections to ensure that they are in the correct position. Thus, the system involves the method of collecting the data from the dots on the face, saving the data, and then "re-marking" the face for the next injection, utilizing a projected image/hologram instead of a 3D printed mask.

FIGS. 1B and 2B illustrate an alternate embodiment of the present invention. In this embodiment, instead of utilizing a smart device to create the 3D representation via photos and patient input where the software is sent to the 3D printer, a medical imaging device such as a three dimensional scanner is utilized. In this system, the patient goes to a designated location where the 3D scanner would create an image of the patient's face/scalp. The physician or technician identifies on the scanned image the locations for the injections in response to the patient's desires, and then the data (image and location marks) is transmitted to a 3D printer which prints a customized mask with the holes formed at the injection sites designated by the physician or technician. The customized mask is then printed with the pre-formed holes for direct injection through the holes, via preloaded syringes or through replaceable syringes as shown schematically in FIG. 3. The mask, as in the embodiment of FIG. 2A can be shipped to the patient or to the practitioner's office. Thus, the method/system of FIGS. 1B and 2B differs from the system/method of FIGS. 1A and 2A in how the data is created and transmitted to the 3D printer. The fluid injection can be in various ways such as depicted in the drawings discussed below.

Figure 2G:
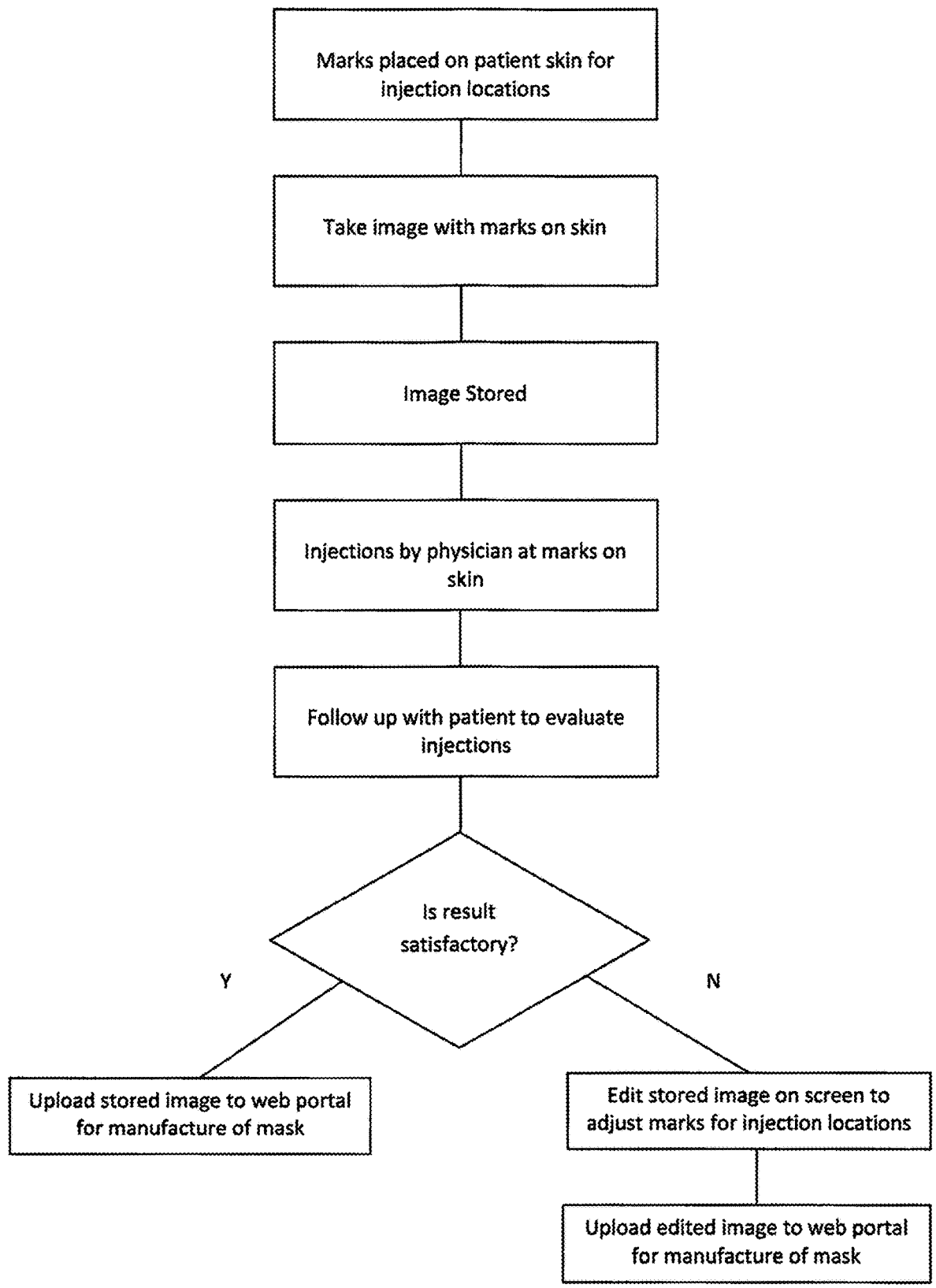
FIG. 2G is a flow chart depicting an alternate system of the present invention.
Figure 2H:
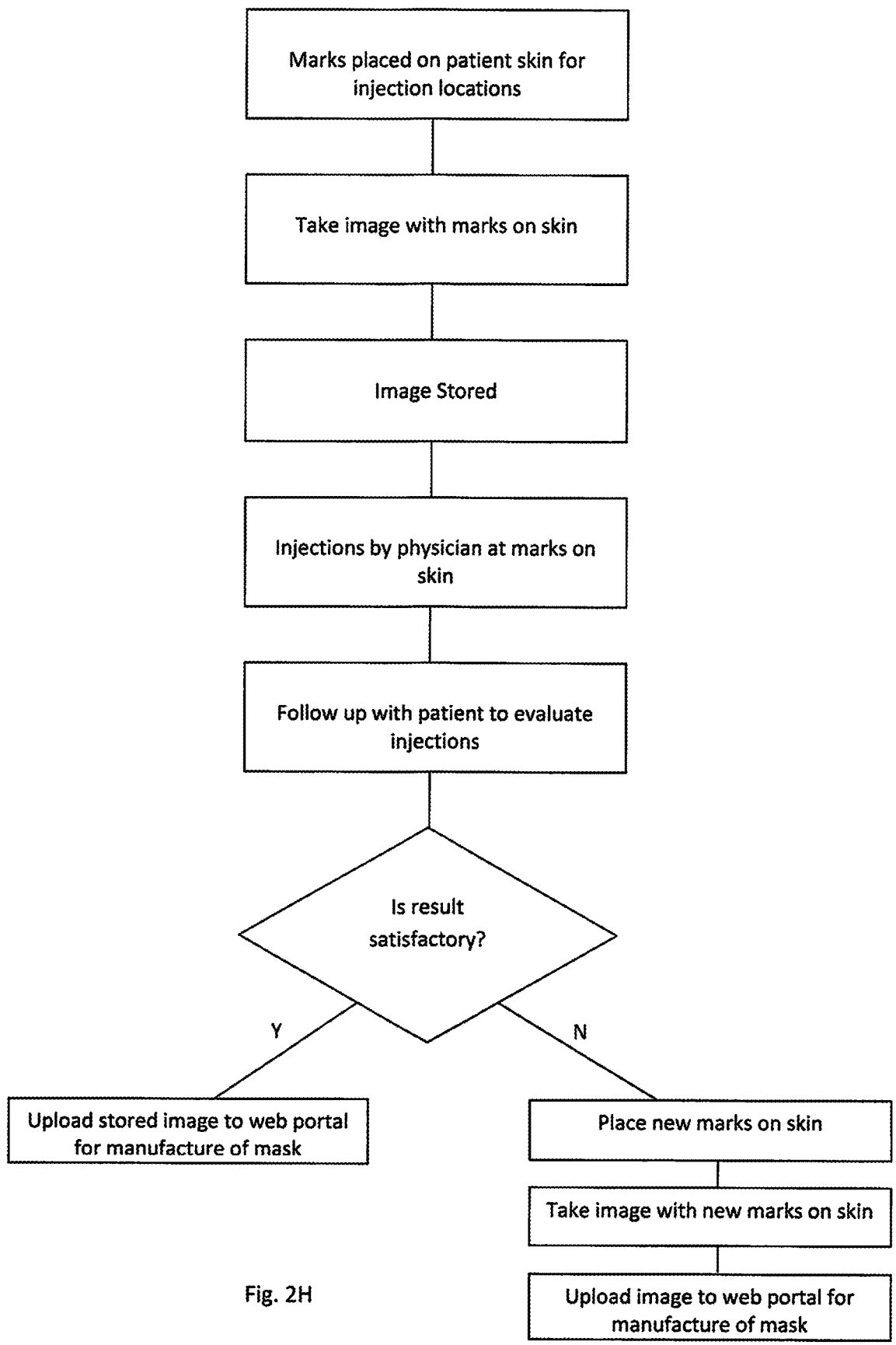
FIG. 2H is a flow chart depicting an alternate system of the present invention.
Figure 21:
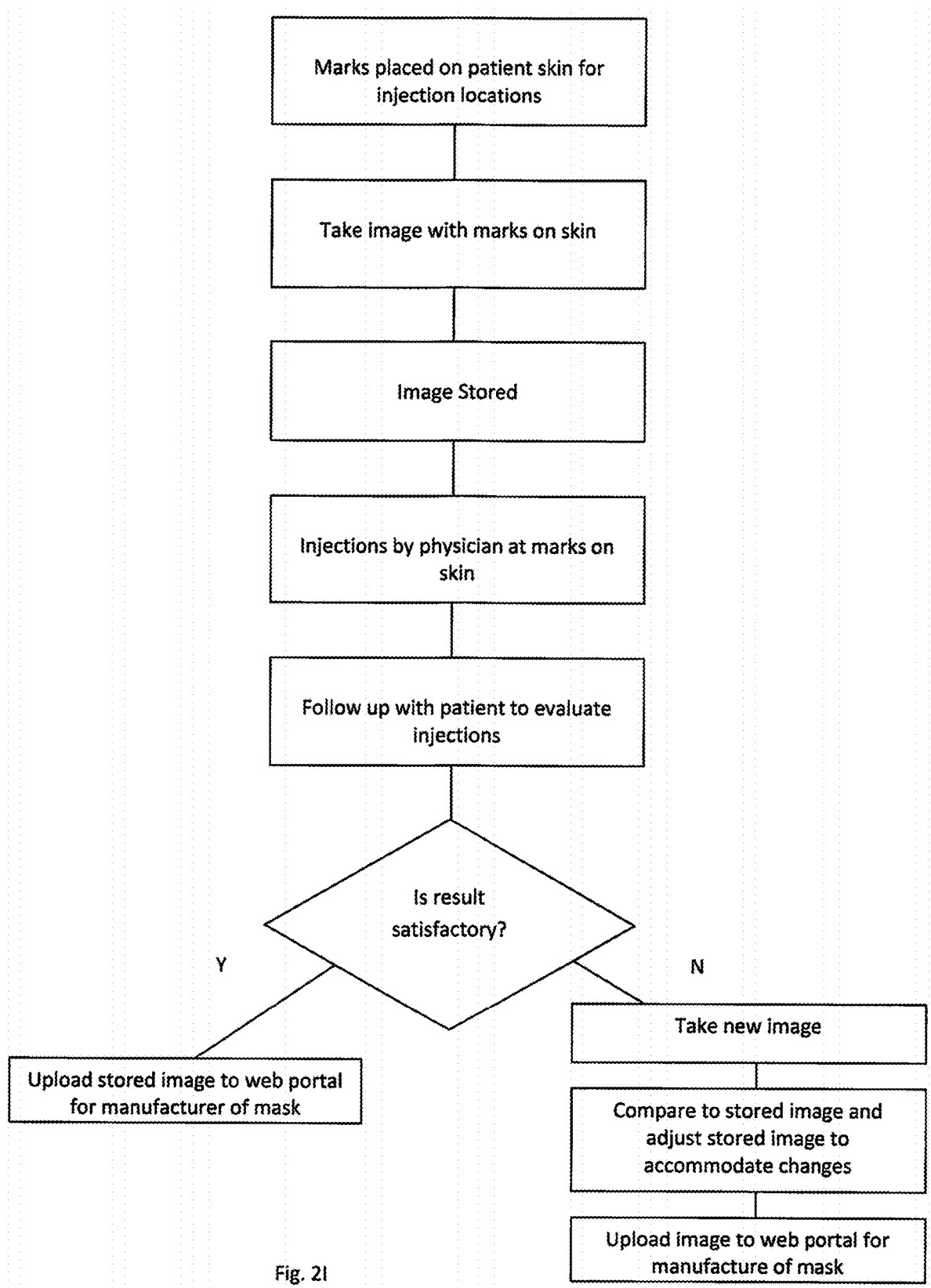
FIG. 21 is a cross-sectional view taken along line D-D of FIG. 20.

Note the customized mask formed in the manner of FIGS. 1B and 2B can in an alternate embodiment, provide holes for the physician to insert a marker to mark the injection locations directly on the patient's skin, and the mask removed so the markings on the patient's skin provide locators for the syringe and fluid injection (as explained in conjunction with FIGS. 2G-2I). In this version, the fluid injections are not conducted through the mask, thereby providing full visibility for the physician during injection.

Thus, in some systems of the present invention disclosed herein, the mask (cover) provides openings (holes) for insertion of injection needles. In alternate systems of the present invention, drug injection is not performed through the mask. Instead, in these alternate systems/methods/processes, the mask (cover) is provided with openings for insertion by the physician, or other health care provider, of a marker or other locating device. In these embodiments, the mask is used to enable markings to be made, then the mask is removed and the physician has direct visualization of the patient's skin as injections are made at the marked locations. In these embodiments, the same mask can be repeatedly used at multiple office visits by the patient so the marks can be made through the mask openings at the same location to provide consistent location of drug injections.

FIG. 2C illustrates an embodiment wherein the physician initially marks the location for injection of Botox (or another drug) directly on the patient. This process/system differs from other processes disclosed herein in that instead of utilizing the 3D image to determine and mark mask opening locations, the opening locations are marked directly on the patient's body, e.g., face of forehead, and then the 3D image is taken with the markings.

More specifically, in this process of FIG. 2C, dots are first placed by the provider, e.g., the physician/clinician, on the patient's skin to designate injection locations and dosing. Next an image (preferably a 3D image) is taken with the marked dots on the patient's body, the dots used as indicators for openings in the customized mask. The injection of the drug, e.g. botulinum toxin, occurs at the marked locations prior to the mask being made. The customized mask is not made until after the botulinum toxin injection has sufficient time for it to fully work, for example 1-2 weeks, to confirm the dots were placed in the correct location. Before making the mask, feedback (and potentially photos) are obtained from the patient or provider (possibly via a questionnaire or input on a mobile app or website) to see how symmetric the result is from the injection 1-2 weeks prior. If the result is satisfactory and symmetric and the patient is satisfied, then the mask will be made based on the markings (dots) on record on the images. If there needs to be a touch-up or the patient is asymmetric, the dots will be moved/changed/added/deleted as needed to give what would be the logical correction of the asymmetry (based on known musculature under the skin). After the correction, either the mask can be made based on the correction or another injection can be made with a 1-2 week follow up to assess the results to see if they satisfy the performance, e.g., cosmetic, objectives. In either event, the customized mask is made in accordance with the methods/processes disclosed herein.

Note in the above process of FIG. 2C, optionally a first image of the patient can be taken before application of the dots to capture the face (or other body region) at rest and potentially in animation without any markings. This could be used for data collection on wrinkles and facial aging over time. This initial 3D image can be taken at the doctor's office or alternatively the patient can take the photos and bring or transmit the photos to the doctor's office.

The flow chart of FIG. 2E provides an example of the mask (cover) holes, rather than providing a site for injection by insertion of a syringe through the holes, provide a locator or guide for physician marking. More specifically, in this embodiment, the customized masks would be made in accordance with the various processes and various configurations disclosed herein, and placed over the patient. The physician then inserts a marker through the holes to mark the injection locations directly on the patient's skin. The mask is then removed, and the markings on the patient's skin provide locators for the syringe and fluid injection. In follow up visits, the mask is again placed over the patient's skin, the physician inserts a marker through the holes to mark the sites, and then the mask is removed and injections are made at the marked locations. Different colored markers can be used to correspond to different dosages and/or different drugs.

FIGS. 2G-2I provide examples of methods utilizing the mask (cover) holes as a guide for physician marking rather than providing for insertion of a syringe through the holes for injection. Note the image(s) can be taken in accordance with the various ways to take images as described herein (e.g., digital photos, scans, etc.), or by other alternative ways. (e.g., symmetric and the patient is satisfied)

Turning first to FIG. 2G, in the first step, markings such as dots made with markers, are manually placed on the patient's skin by the physician (or other health care provider) to provide locators for drug injection, e.g., injection of botulinum toxin. An image is then taken of the patient's skin, e.g., face, with the markings. The image is stored for later evaluation. The drug is then injected into the patient at the regions of the markers on the skin. The patient then waits a select period of time, two weeks by way of example, then returns to the physician. At this point, the physician can evaluate the results of the first treatment by the initial injection. If the results are satisfactory (e.g., symmetric and the patient is satisfied), the first stored image is uploaded to a web portal for manufacture of the 3D mask (or alternatively transmitted directly for manufacture of the mask). On the other hand, if the result is not satisfactory (e.g., there needs to be a touchup or the patient is asymmetric and the markings, e.g., dots, need to be moved/changed/added/deleted), the first stored image is edited on the screen and the location of the markers (e.g., dots) are adjusted accordingly. Once adjusted, the edited image is uploaded to the web portal for manufacture of the 3D mask (or alternatively transmitted directly for manufacture of the mask). Note the images can be taken in accordance with the various methods disclosed herein, with the software application (app) enabling editing, processing and formatting the image for 3D printing (or other forms of manufacture).

In the alternate embodiment of FIG. 2H, the steps are the same as the method of FIG. 2G, except a second image is taken of the edited markings. More specifically, in the first step, markings such as dots made with markers, are manually placed on the patient's skin by the physician (or other health care provider) to provide locators for drug injection, e.g., injection of botulinum toxin. An image is then taken of the patient's skin, e.g., face, with the markings. The image is stored for later evaluation. The drug is then injected into the patient at the markers on the skin. The patient then waits a select period of time, two weeks by way of example, then returns to the physician. At this point, the physician can evaluate the results of the first treatment by the initial injection. If the results are satisfactory, the first stored image is uploaded to a web portal for manufacture of the 3D mask. On the other hand, if the result is not satisfactory, new markings are made on the skin and a second image is taken to replace the first stored image. This new second image is uploaded to the web portal for manufacture of the 3D mask. Note the images can be taken in accordance with the various methods disclosed herein, with the software application enable editing, processing and formatting the image for 3D printing.

The markings in the foregoing embodiments can be made at a non-rest position such as raised eyebrows, frown, etc. and then the later evaluation can also be made at the non-rest state. The image, e.g., scan, can be taken at a rest state in some embodiments.

In the foregoing embodiments either the first image is edited if necessary or a second replacement image is taken. In an alternate embodiment, depicted in FIG. 2I, comparative images are taken. In this different approach, if the initial results are not satisfactory, a second image is taken and compared to the first image and the software's comparative analysis produces a desired image for the mask printing by editing (adjusting) the first image. More specifically, as shown in the flow chart, in the first step, markings such as dots made with markers, are manually placed on the patient's skin by the physician (or health care provider) to provide locators for drug injection, e.g., injection of botulinum toxin. An image is then taken of the patient's skin, e.g., face, with the markings. The image is stored for later evaluation. The drug is then injected into the patient at the markers on the skin. The patient then waits a select period of time, two weeks by way of example, then returns to the physician. At this point, the physician can evaluate the results of the first treatment by the initial injection. If the results are satisfactory, the first stored image is uploaded to a web portal for manufacture of the 3D mask. On the other hand, if the result is not satisfactory, a second image is taken and compared to the first stored image. This stored image is adjusted based on the new image and is uploaded to the web portal for manufacture of the 3D mask. Note the images can be taken in accordance with the various methods disclosed herein, with the with the software application enable editing, processing and formatting the image for 3D printing.

Figure 2J:
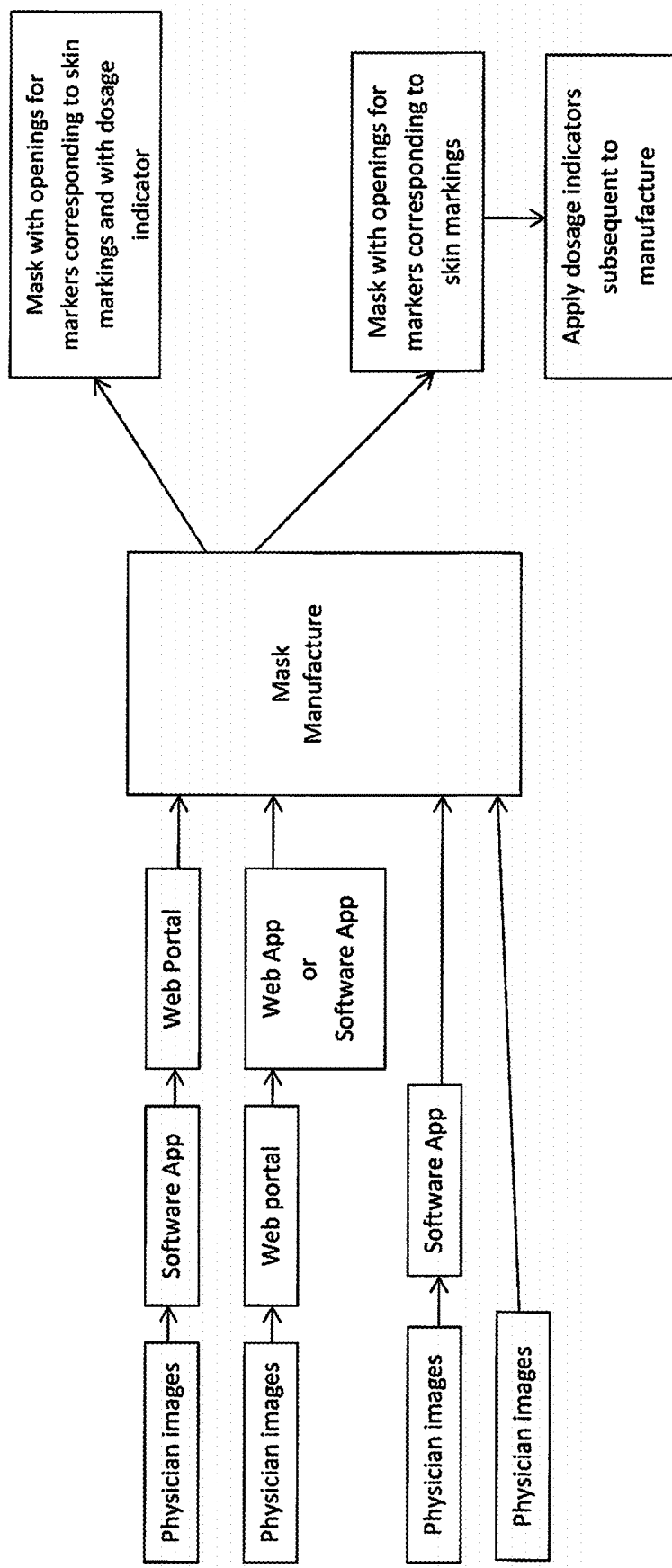
FIG. 2J is a block diagram depicting manufacture of the cover in accordance with some embodiments of the present invention.

FIG. 2J provides a diagram showing the process of mask manufacture for the methods of FIGS. 2G-2I. In this diagram, the mask is made by 3D printing, however, it should be appreciated that the mask can be made by other ways as disclosed herein. The physician's images of the patient with markings as locators for injections are uploaded to a web portal. Based in these image(s), the manufacturer creates/manufactures the mask such as via 3D printing. The mask is made with holes corresponding to the markings on the skin. The mask can be made with dosage indicators adjacent the holes. Alternatively the dosage indicators are applied to the mask adjacent the holes after manufacture. In either case, the holes in the mask are dimensioned to accommodate a marker therethrough so the physician can mark the skin through the holes then remove the mask for injection at the markings. With the dosage indicators on the mask, the physician can insert different colored markers to correspond to the different dosages to mark the skin prior to removal of the mask for injection.

Note the diagram of FIG. 2J shows the alternative where images can be created and formatted and sent directly to a mask manufacturer without use of the portal.

Note the images can be processed and formatted by a software application downloaded independent of the web portal e.g., on a mobile device or desktop. The images are then uploaded to the portal for access by the manufacturer, e.g., printer of the mask, or in alternate embodiments, sent directly to the manufacturer. Alternatively, the images can be processed and formatted via a web app accessible on the web portal where it is subsequently uploaded for access by the manufacturer. (The web portal can be designed to block access to the software by the manufacturer and only allow access to the formatted images for manufacturing e.g., printing). Stated another way, the customized cover can be manufactured from a set of instructions provided from a software based application processing an image of an anatomical view of the patient made with the marked locations thereon. The cover is customized to the portion of the body based on the software based application and the plurality of openings in the cover are customized to the desired locations of markings through the cover for subsequent injection of one or more drugs independent of the cover, i.e., with the cover removed. The software based application can be downloaded to a computer or mobile device for the physician. In other embodiments it is accessed or downloaded through the web portal. In other embodiments, the physician sends the images to the manufacturer that accesses or downloads the app.

In some embodiments, the mask can be manufactured so that the openings accommodate markers but do not accommodate injection devices. For example, a cloth or other material can be provided at the openings through which a marker can be inserted but an injection device could not safely be inserted. Other structure or configuration is also contemplated in these embodiments for contraindication and/or prevention of injection through the openings.

Note in an alternate process of FIG. 2C, instead of first injecting the drug with 1-2 week follow up, after the markings are made and images taken, the mask can be made so that the first injections are through the mask. This is a different approach since injections are made through the mask without direct visibility. Also, in the approach, the mask would need to be made with openings that can accommodate injection devices.

In the above process, coding, such as color coding and/or number/symbol coding, of marked locations before the 3D scan is taken can be made to designate units to be embossed or applied as stickers to the mask mold. More specifically, when the physician/provider is marking the patient's face (or other body region) with dots to show the locations of the drug injections, e.g., botulinum toxin injections, they can use different colored markers/pencils to designate different doses based on a predetermined key. For example, red dots can signify a dose of 4 units and black dots can signify a dose of 2 units of the drug to be later injected through the mask. (Other dosage and other color or symbols are also contemplated). Then the 3D photo is taken with the dots on the body which is translated into the hole (opening) locations on the mask. The number of units for the dots will then be designated on the final printed mask, either with engraving, embossing, stickers, or different color resin (if the mask is made of resin) around each opening in the mask. The designations can be made with and integral with the mask or provided on the mask after manufacture, e.g., printing. This will be the dosing guide for the provider injecting later with the mask in place or for injecting at the markings with the mask removed in alternate approaches disclosed herein. Such coding to indicate dosage can also be utilized in the embodiments wherein the patient is injecting the drug.

In an alternate embodiment, the physician is fully out of the loop and the patient deals directly with a centralized location to obtain the mask and syringes, preferably, pre filled. The centralized location can be one or more company locations which print the masks in response to patient input and provide the drugs/medicines directly to the patient so the patient can inject the drug. The specific steps of this embodiment are depicted in FIG. 2D as follows. The patient takes photos outside the doctor's office, the patient answers questions on the app of the smart device regarding appearance objectives, and the photos with the inputted data are sent to a central location (e.g., a company). Dots are placed on the images via the algorithm (in accordance with the patient input) at the central location and the 3D model is created and the customized mask is printed with the injection holes corresponding to the dots. The customized mask is then sent to the patient with syringes, either separate from the mask or attached to (or integral with) the mask, and which can be preloaded with the fluid or empty and sent with the fluid, for injection by the patient. As can be appreciated, in this method/system, the patient interacts directly with a central location, leaving the physician out of the loop. Since multiple injections are provided over a period of time, additional preloaded syringes, or additional syringes and additional fluid, can be periodically sent to the patient for injection through the same customized mask. The patient's progress can be continuously or periodically visually monitored or via analysis of additional photos. Note guide channels for the syringes in accordance with the embodiments discussed herein can facilitate injection by the patient.

The diagram of FIG. 4 illustrates schematically the option of the system wherein the customized mask can be shipped to the physician or to the patient, as shown by the split line in the diagram. Such option is also applicable to the 3D scanner embodiment of FIG. 2B and other embodiments disclosed herein. More specifically, as can be appreciated from the diagram, the patient takes photos, answers questions regarding objectives, and uploads the photos to the app wherein the software provides a 3D representation of injection locations. The customized mask is printed from the 3D representation and shipped either directly to the patient or alternatively directly to the physician as described herein.

To facilitate imaging, a chinrest or other facial support for aligning the face and preventing movement can be utilized to get a proper 3D image.

As disclosed herein, the customized mask of the various embodiments disclosed herein are made by 3D printing process. However, it should be understood that the customized masks of the present invention can alternately be made by other processes such as injection molding, hand made, etc.

FIGS. 5-11 illustrate various embodiments of the customized masks of the present invention by way of example, it being understood that masks of other shapes and sizes and covering other sections of the face or scalp (or other body regions) could be provided. Additionally, it should be appreciated that since the holes formed in the masks would vary from patient to patient, the holes illustrated in the masks of FIGS. 5-11 are shown by way of example since the number and location of holes would vary from patient to patient (mask to mask).

Figure 5A:
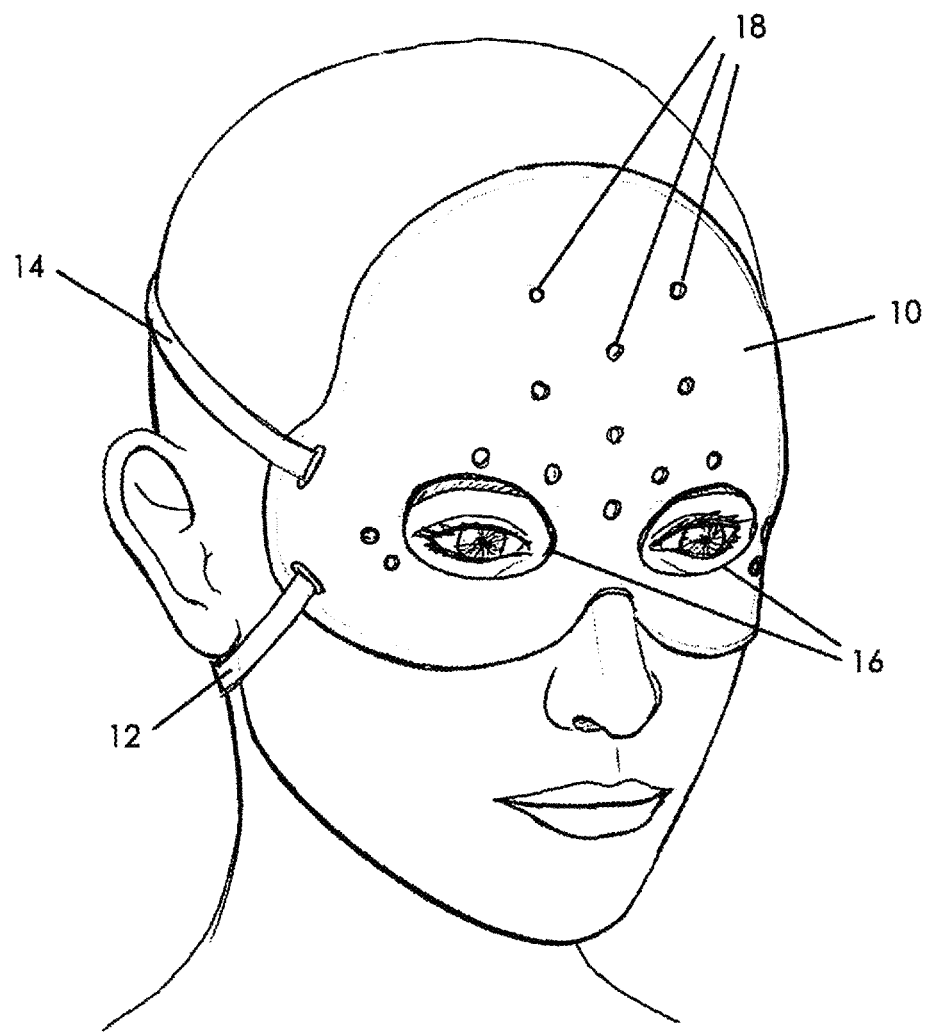
FIG. 5A is a front perspective view of one embodiment of a customized forehead and lateral eye mask (cover) of the present invention with preformed holes.

FIG. 5A shows a first embodiment of a customized mask in the form of a forehead and lateral eye mask. These are the most common areas injected with botulinum toxin. The customized mask, produced by 3D printing as described above (or produced by other methods), reduces variability and is reproducible by providing custom masks of the forehead and sides of their eyes (crow's feet area). The mask is designated generally by reference numeral 10 and has face and eye slits (openings) 16. Mask 10 includes straps 12, 14 extending around the head to help secure the mask to the patient's face, although other securement devices for mask 10, as well as for other masks disclosed herein, are also contemplated which can include, belts, Velcro, hooks, clasps, etc. The mask 10 aligns with the patient's eyebrows and also the midline of the nose. The pre-formed (pre-drilled) holes 18 (only a few of which are labeled for clarity) are provided in the printed mask 10 to provide locators or guides for fluid injection via syringes or other fluid injection devices placed into the holes to access the desired regions of the patient's forehead and face.

Figure 5B:
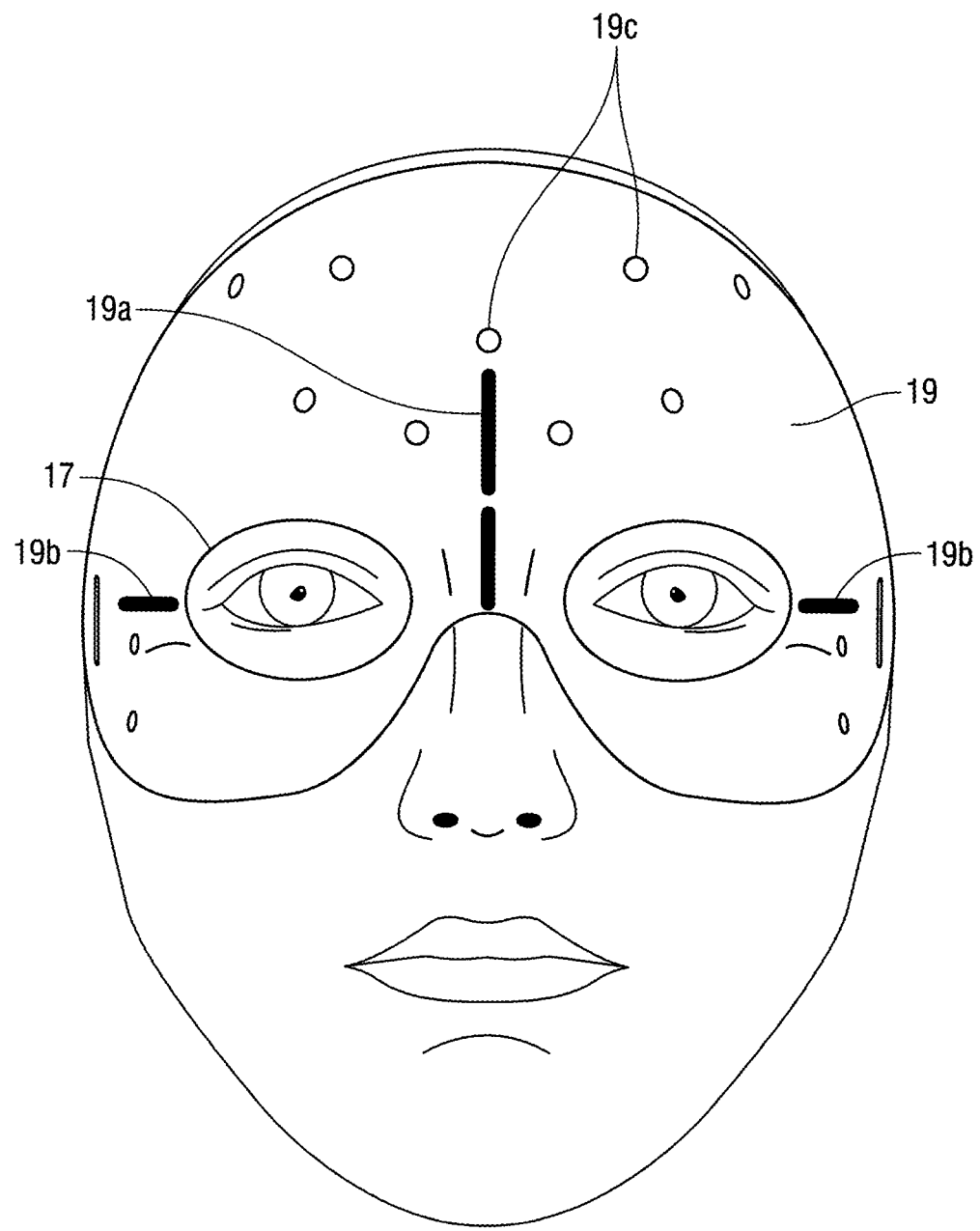
FIG. 5B is a front perspective view of an alternate embodiment of a customized mask of the present invention having alignment lines.

FIG. 5B illustrates an alternate embodiment of a forehead and lateral eye mask having overlaid vertical alignment line 19a and overlaid horizontal alignment line 19b on mask 19 for the nose to mark the midline of the mask 19 and lateral canthus to mark vertical orientation. That is, the alignments lines 19a, 19b help to center the mask 19 relative to the bridge of the nose and eyebrows with one line 19a down the middle of the nose for aligning side to side and lines 19b at the outer edge of the eyes to align up and down. Note such alignment lines can be provided, e.g., overlaid, on the other masks disclosed herein. The mask 19, like mask 10 of FIG. 5A, has eye slits and a strap (not shown), or other securement mechanism, to hold mask 19 on the patient's face and forehead. Holes 19c provide injection site locators in the same manner as holes 18 of FIG. 5.

Figure 5C:
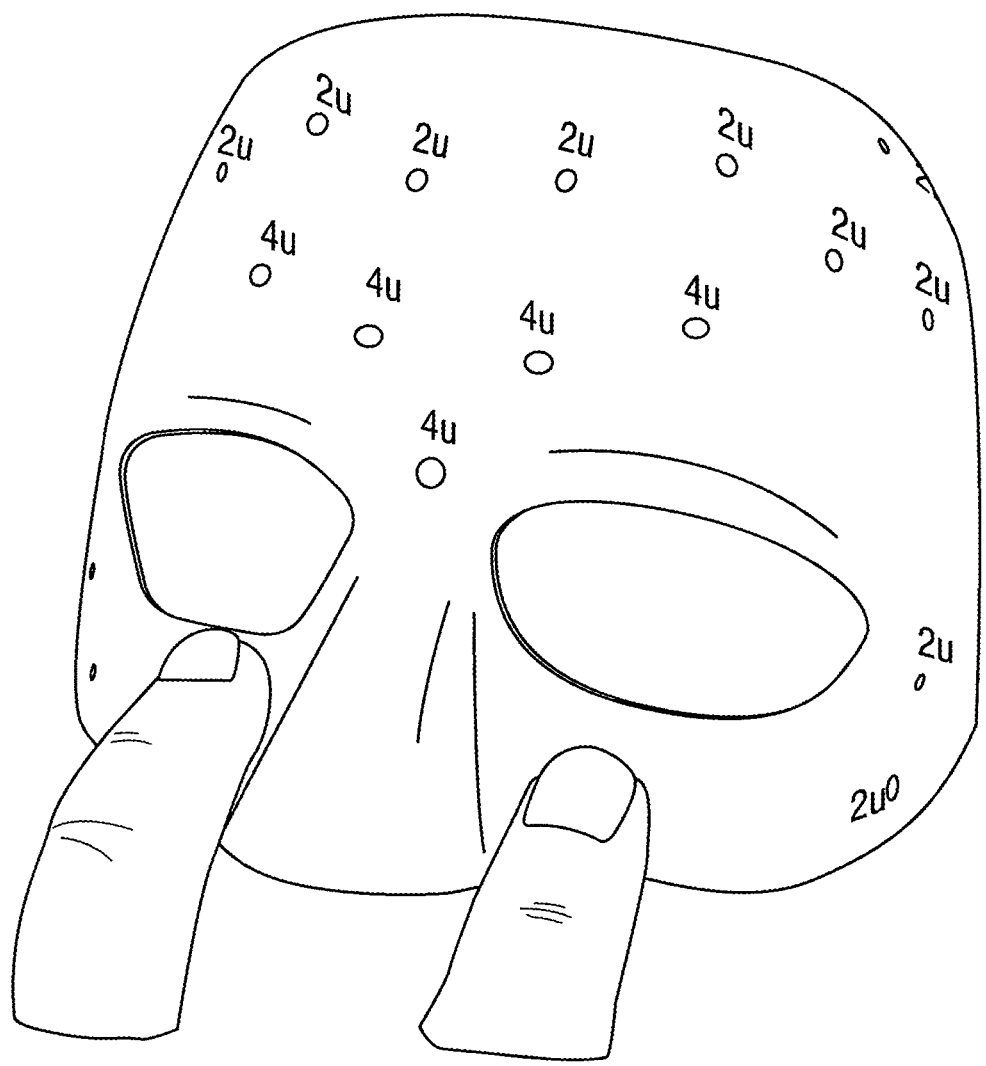
FIG. 5C is a perspective view of an alternate embodiment of the cover of the present invention having dosage indicators.

FIG. 5C illustrates an alternate embodiment of the mask with a central (midline) alignment marker between the eye openings and dosage designations, e.g., 2µ and 4µ.

Figure 6:
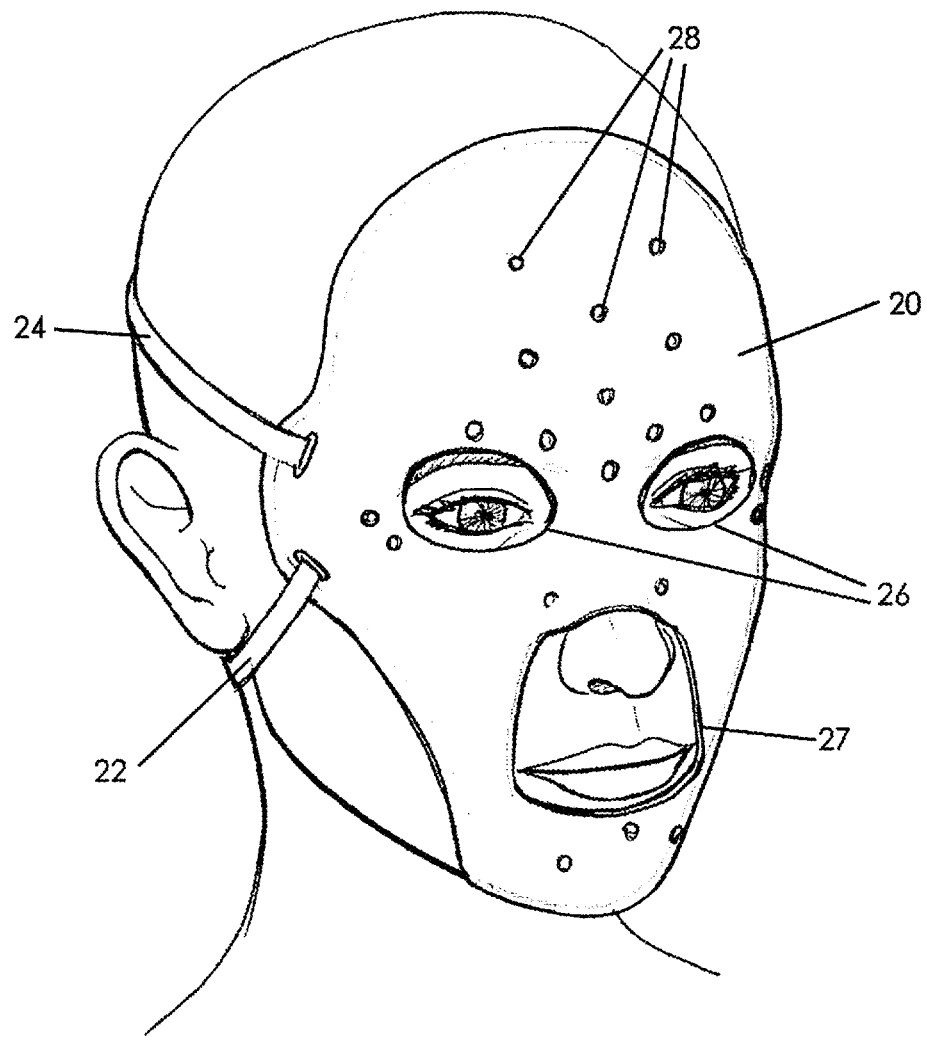
FIG. 6 is a front perspective view of an alternate embodiment of a customized full face mask of the present invention.
Figure 7B:
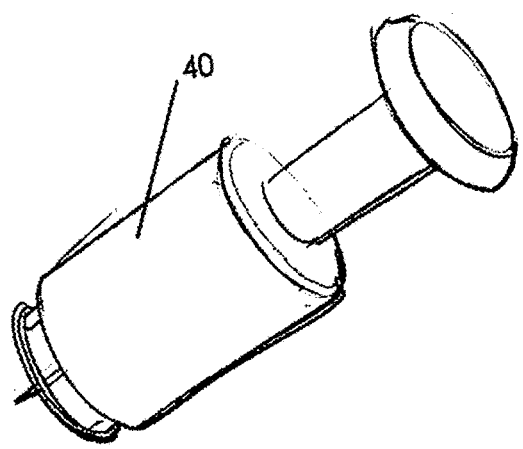
FIG. 7B is a perspective view of the mini-syringe used with the mask of FIG. 7A.
Figure 7A:
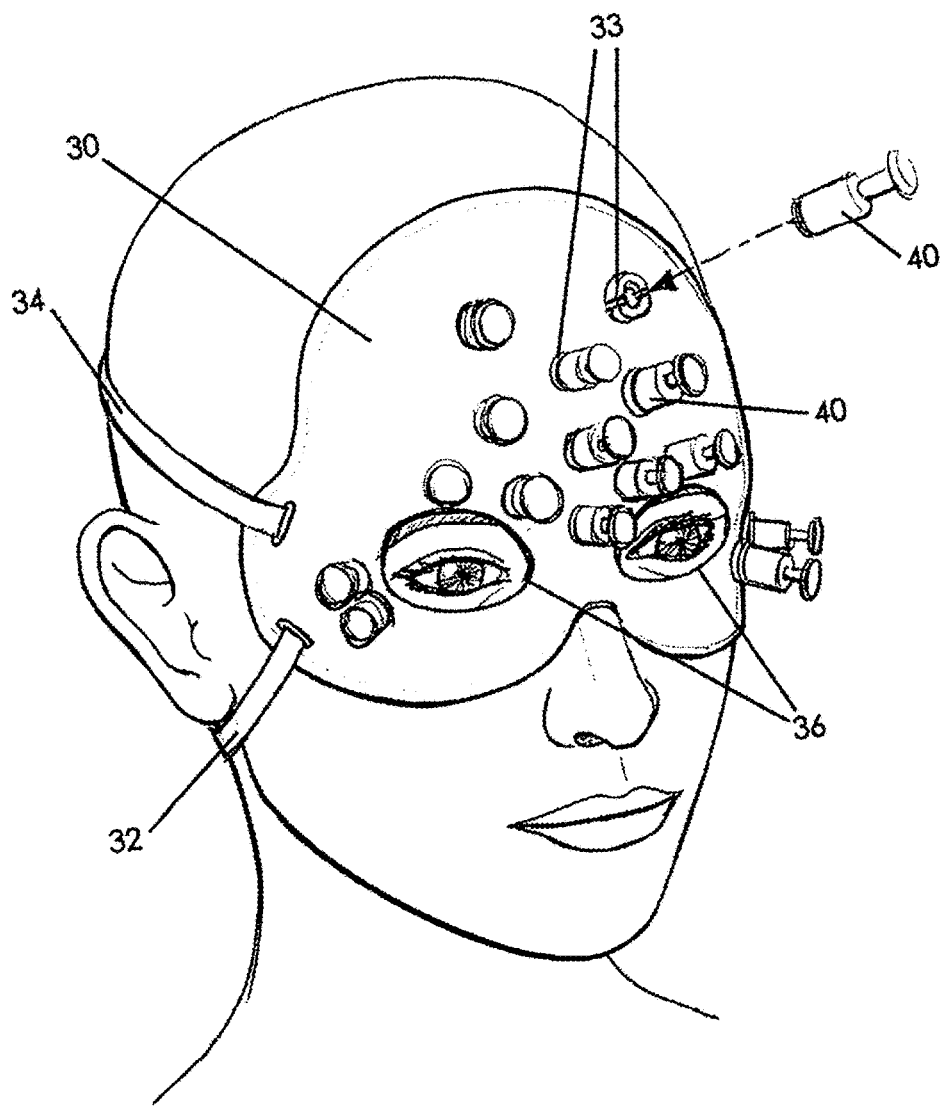
FIG. 7A is a front perspective view of another alternate embodiment of a customized forehead and lateral eye mask of the present invention having replaceable mini-syringes attachable/mountable to the mask.

FIG. 6 illustrates an alternate embodiment of the mask forming a full face mask. Mask 20 is in the form of a full face mask with eye slits (openings) 26 and mouth and nose slits (openings) 27) and includes straps 22, 24 extending around the head to keep the mask 20 in place. Pre-formed holes (injection spots/locations) 28 for the forehead, lateral eyes, nose, perioral and other regions of the face are provided. As in the embodiment of FIG. 5A, the pre-formed (pre-drilled) holes 28 are provided in the printed mask 20 to provide locators for fluid injection via syringes or other fluid injection devices placed into the holes 28 to access the desired regions of the patient's forehead and face. Note for clarity, in this and in other embodiments, only a few of the holes are designated with a reference numerals.

In the embodiments described herein, straps, elastic bands, or other mechanism, can be provided to hold/secure the mask to the face. The masks can include for example nasal or chin fixation structures or forming the mask so it extends down to the chin or down the nose for additional securement. That is, the mask can be formed to extend to cover bony fixation points to enhance securement.

FIGS. 5A, 5B and 6 show pre-formed holes wherein the physician would insert syringes or other injection devices directly through the holes for injection. In the alternate embodiment of FIG. 7, instead of the pre-formed holes to receive standard syringes, replaceable mini-syringes are attached to the syringe mounts 33 for multiple use. More specifically, forehead and lateral eye mask, designated generally by reference numeral 30, has a series of syringe mounts 33 extending outwardly from the mask 30 for attachment of syringes 40. The syringe mounts 33 aid alignment, e.g., centering, of the syringes to enhance accuracy and consistency of injection. Syringe 40 includes a needle and plunger for fluid injection. Syringe 40 is shown as one type of injection device that can be attached to the syringe mount 33. The mounts (receivers) 33 are at the desired (pre-selected) regions of injection and can be configured to enable snap on attachment, screw on attachment or other methods of attaching the syringes 40 to the mask 30. The syringes are preferably pre-loaded (pre-filled) but alternatively can be empty and require filling with fluid prior to injection. The mask 30 is in the shape of mask 10 of FIG. 5 with straps 32, 24 and eye slits (openings) 36. It should be appreciated that the mounts for the syringes is shown on mask 30 by way of example but can be provided on mask 20 or on other masks disclosed herein.

Figure 8:
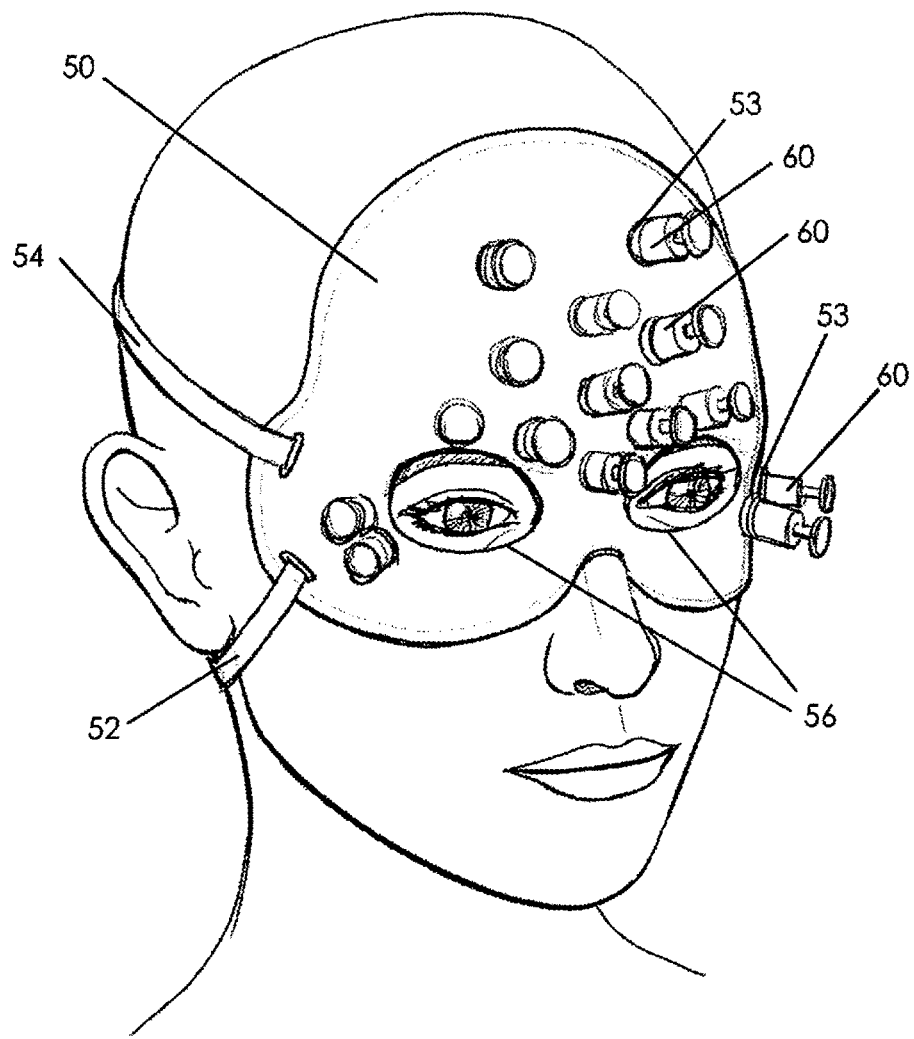
FIG. 8 is a front perspective view of another alternate embodiment of a customized forehead and lateral eye mask of the present invention having pre-loaded syringes attached to the mask.

In the alternate embodiment of FIG. 8, instead of the predrilled holes of FIG. 5A to receive standard syringes, pre-loaded syringes (or other injection devices) are provided already mounted to the mask or built into the mask itself. More specifically, forehead and lateral eye mask 50 has as series of syringe mounts 53 extending outwardly from the mask 50 for securing syringes 60 (or other injection devices), preferably pre-filled (only some of which are labeled for convenience). The mounts (receivers) 53 are at the desired (pre-selected) regions of injection and the syringes 60 are snapped on, screwed on or attached by other methods of attachment for the syringes prior to shipment of the mask 50. In the built in version, the syringes can be non-removably attached to the mask 50. The syringe buttons can be pushed so the needles go in and then automatically retract. The mask 50 is in the form of mask 10 with straps 52, 54 and eye slits (openings) 56. It should be appreciated that the already mounted or built in syringes are shown on mask 50 by way of example but can be provided on any of the other masks disclosed herein.

To facilitate insertion of the syringe into the preformed holes in the mask, syringe guide channels can be provided on the mask. The guide channels (also referred to herein as "channel guides" or "guides") align the syringe to center the syringe to thereby center the injection. For example, if there is a 4 mm hole in the mask, the needle can be aimed upwards, downwards or sideways which will change the injection area. These guides ensure the syringes inserted through the mask are kept straight which provides more control and consistency of injection. These guide channels attach to the mask in different ways as described below. The guide channels provide a way to align the syringe without having the needle get in the way, without utilizing a self-advancing and self-retracting mechanism for the needle. These guide channels can be integral (monolithic) with the mask or alternatively separate components attached or secured to the mask. In either case, the guide channel openings are aligned with the pre-formed holes in the mask so the syringe needle can be inserted through the guide channel and mask for injection of the fluid into the patient's body. The guide channels can provide guides for conventional syringes or for the designed syringes disclosed herein, which can in some embodiments be prefilled. An example of such guide channels was discussed above in conjunction with mask 30 of the embodiment of FIG. 7. Various alternate embodiments of the integral and separate syringe guide channels are discussed below in reference to FIGS. 12A-48.

Turning initially to FIGS. 12A-12D and 13-17, a syringe guide channel 106 is illustrated. The guide channel 106 (also referred to herein as a "channel guide") extends upwardly (proximally) from the upper surface 104a (also referred to herein as top or proximal surface) of the mask 104. As shown, the designated region 104 is a section of the overall mask cutaway for illustrative purposes (see detail A-A of FIG. 12A) since in this embodiment, the guide channels are separate components attached to the mask 104. Note that two guide channels are shown in the cutaway region 104a of the mask 104 in FIG. 12B and a single guide channel is shown in the region 104a in FIG. 12D, it being understood that a different number of guide channels can be provided for securement to the mask 104. The number of guide channels, in this and in alternate embodiments disclosed herein, preferably correspond to the number of pre-formed holes in the mask. The guide channel 106 is shown cylindrically shaped, although other shapes/configurations and sizes are also contemplated.

Guide channel 106 is inserted into, e.g. pressed into, the preformed hole 116 of mask 104. The guide channel 106 helps to align the syringe to center the injection. Guide channel 106 includes a proximal opening 114 communicating with the lumen extending through guide channel 106. Guide channel 106 can be flexible and is inserted through the hole 116 of the mask 104 so circumferential cutout 112 (FIG. 17) is engaged by the circumferential wall of the hole 116, with lower (bottom/distal) portion 113 forming a flange or stop to prevent separation of the guide channel 106 from the mask 104. With the guide channels 106 provided as separate components, they can be provided sterile and removed from the mask and discarded after use. Also, by being provided as separate units, they can be interchanged with guide channels of different sizes, shapes, depths, etc. For example, if a greater depth of injection is required, a guide channel to accommodate such increased depth can be inserted.

The top surface 106a of guide channel 106 forms a stop for the injection syringe, e.g., syringe. More specifically, the syringe, designated by reference numeral 102, has a flange 103 and a plunger 105 movable distally to inject the fluid stored in the chamber 113 of the barrel 115 of the syringe 102. Plunger 105 supports a needle 108 with a penetrating tip so that distal movement of the plunger 105 injects the fluid from the syringe. Seal 109 seals off the inside of the syringe as the plunger 105 is pressed to deliver the medication.

Note in alternate embodiments, a mechanism can be provided to provide retractability of the syringe needles.

Figure 15:
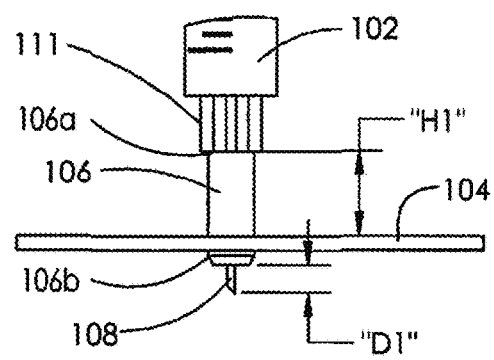
FIG. 15 is a close up view of the area of detail B of FIG. 13.
Figure 16:
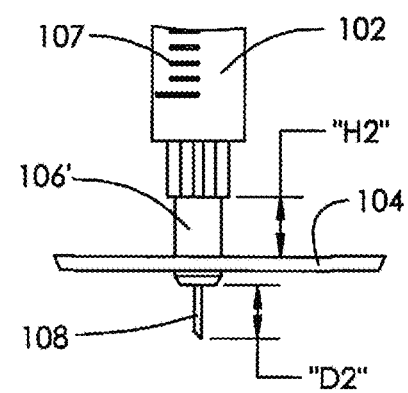
FIG. 16 is a close up view similar to FIG. 15 showing an alternate embodiment of the syringe guide channel of the present invention.
Figure 22A:
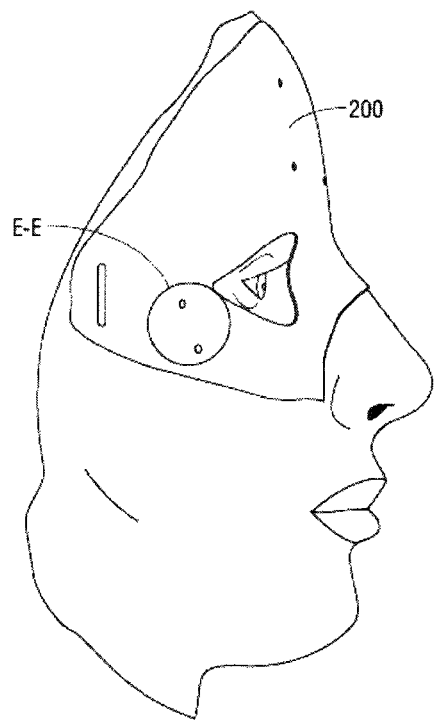
FIG. 22A is side perspective view of a mask in accordance with an alternate embodiment of the present invention.
Figure 22B:
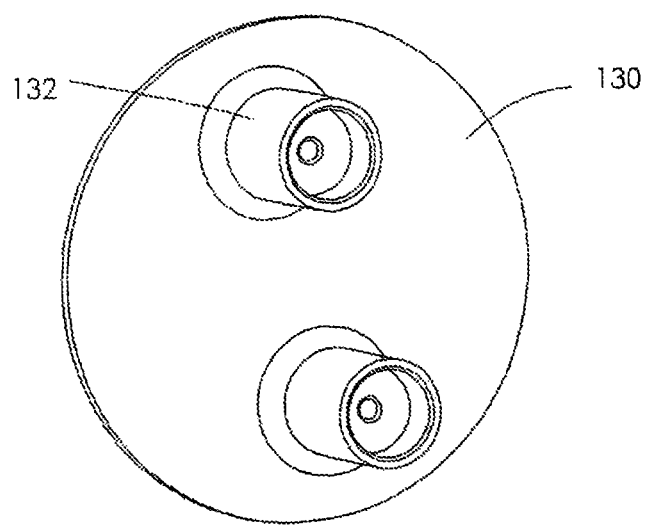
FIG. 22B is an enlarged view of the area of detail B-B identified in FIG. 22A showing the guide channels in accordance with an alternate embodiment of the present invention.
Figure 22C:
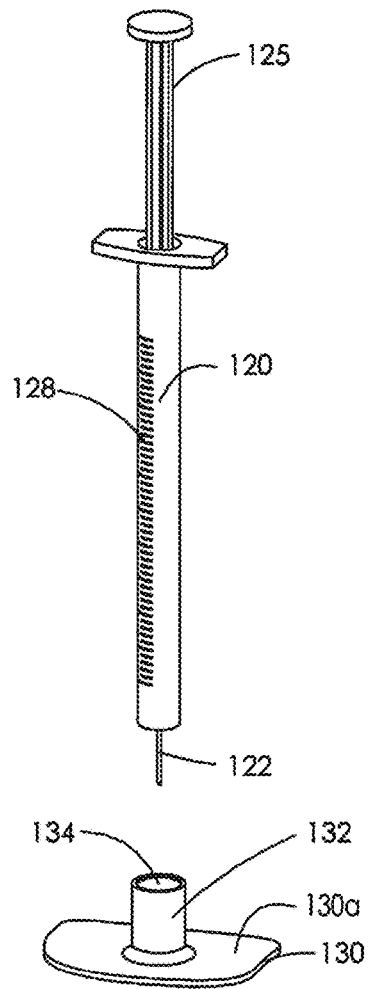
FIG. 22C is a perspective view showing a syringe prior to insertion into the syringe guide channel (extending from a portion of the mask) of FIG. 22B.
Figure 23:
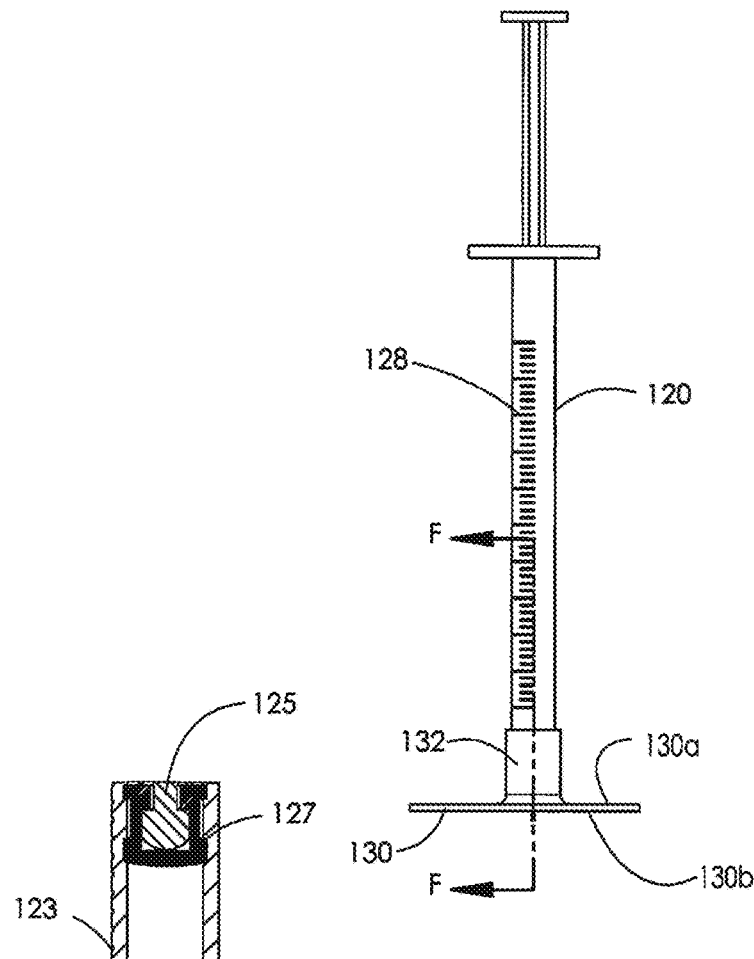
FIG. 23 is a front view showing the syringe inserted into the guide channel of FIG. 22, the needle shown in the retracted position.
Figure 24:
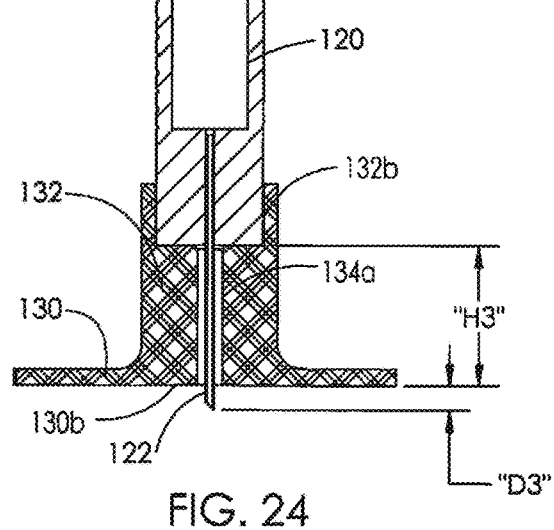
FIG. 24 is a cross-sectional view taken along line F-F of FIG. 23.
Figure 25:
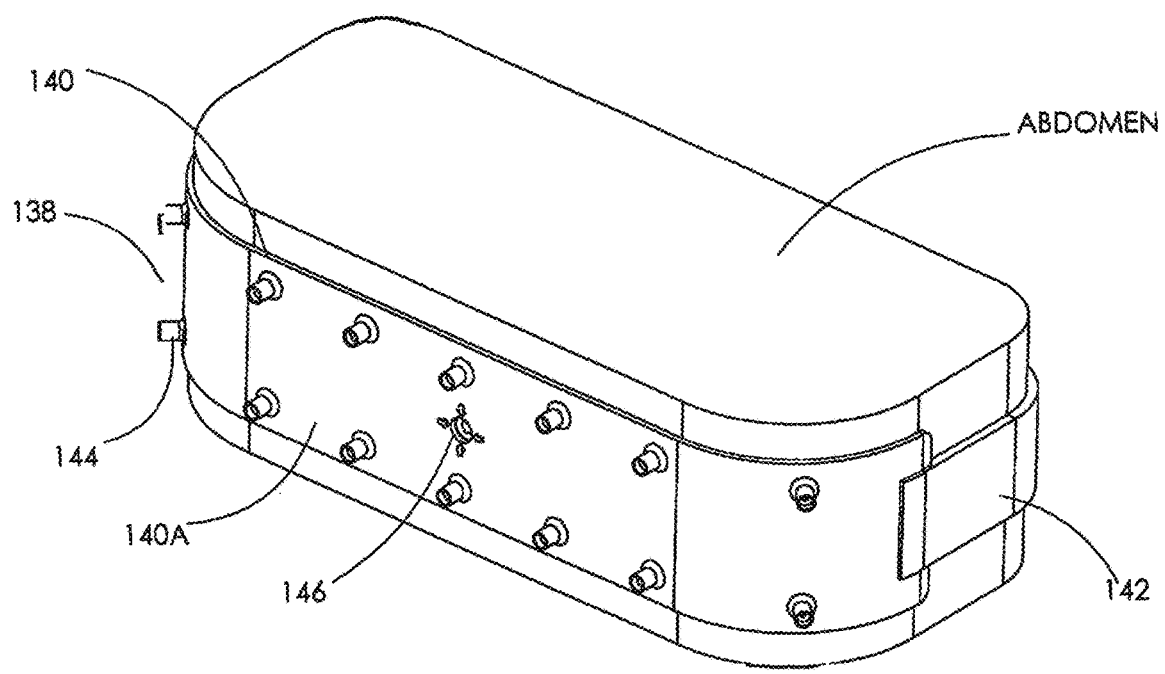
FIG. 25 is a front perspective view of an abdominal mask (cover) of the present invention shown wrapped around a portion of the patient's body.
Figure 26:
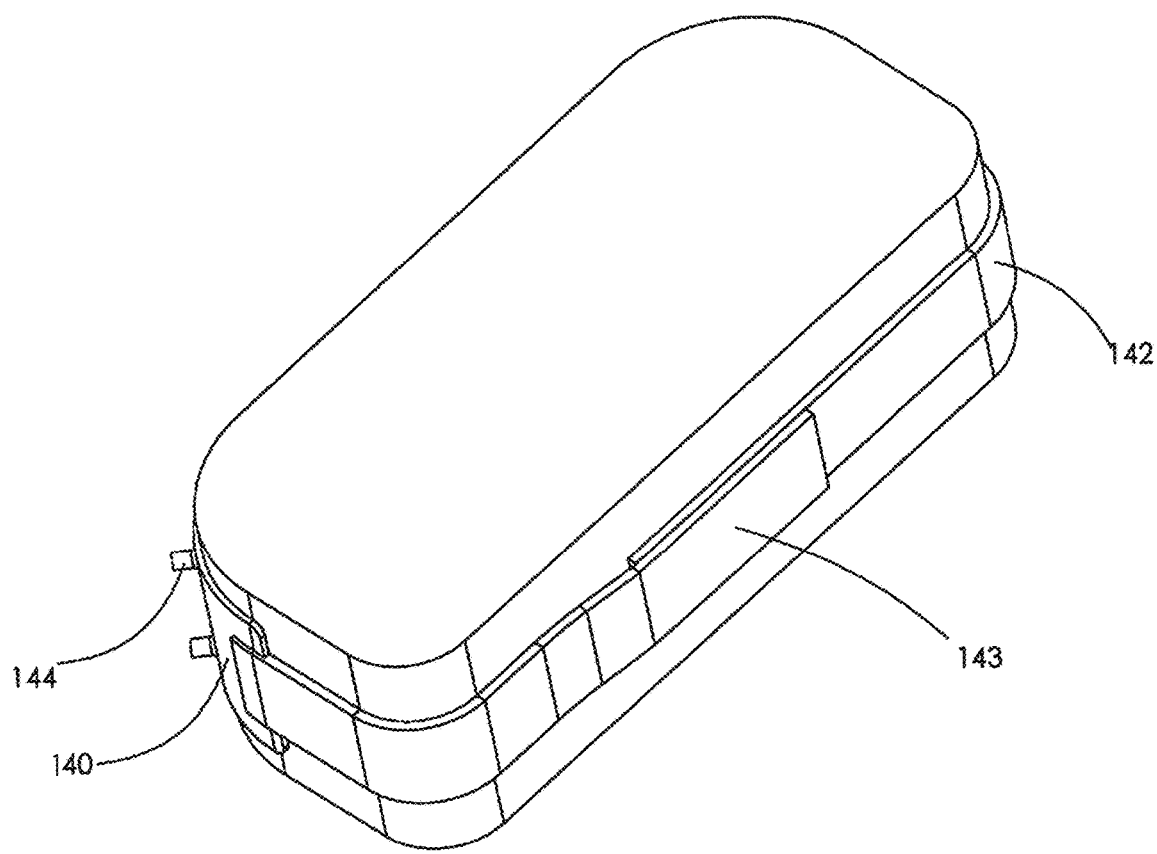
FIG. 26 is a rear perspective view of the abdominal mask of FIG. 25 showing the closed strap.

The height of the guide channel 106 in this embodiment controls the depth of injection. This can be appreciated by comparing FIGS. 15 and 16. A taller guide channel having a height H1 as shown in FIG. 15 yields a shallower injection depth D1 while a shorter guide channel 106' having a height H2 as shown in FIG. 16 yields a deeper injection depth D2. These depths can be customized for different patients or arranged in specified arrays for deeper injections in certain areas and shallower injections in other areas. By adjusting the height of the channel guides, the depth of injection can be controlled without changing any structure of the syringe. However, it is also contemplated, that alternatively, the injection depth can be controlled by modifications to the syringe, e.g., the distance the needle extends distally through the mask as a result of the syringe structure. For example, various gauge and needle lengths can be used to deliver medication deeper or more superficial.

In use, the syringe guide channels 106 are each inserted into one of the preformed holes in the mask 104 to thereby anchor it to the injection site. (Note alternatively the mask can be provided with the removable guide channels already positioned in the mask). The syringe 102 is then inserted through openings 106 in the guide channel 104. The syringe 102 is inserted until the distalmost wall of distal portion 111 contacts (abuts) the upper (proximal) surface 106a of guide channel 106. This depth is designated by D1. Thus, the guide channel 106 provides a stop for syringe insertion and thus controls the depth of insertion of the needle to control the depth of injection. When attached to the guide channel 106, the needle 108 extends through the lumen of the guide channel 106 and past distal surface 104b of the customized mask 104 and past distal surface 106b of guide channel 106. To inject the fluid, the plunger 105 is depressed, thereby injecting the fluid, e.g., medicine or drug, into the predesignated injection locations for the patient previously determined and located by the pre-formed customized patient mask created in the processes discussed above. Markings or graduated lines 107 can be provided on the outer wall of the barrel 115 for dosing, i.e., to track the amount of fluid in the syringe 102. Alternatively, the syringes can be color-coded to indicate dosing without the use of the markings or can be prefilled or pre-calibrated with the required dose. Such markings, color coding or pre-filling can be utilized with the other syringes disclosed herein. An insulin type syringe can also be calibrated for exact dosage to be used for injections at designated locations or holes. The syringe could come pre-filled or re-fillable. The exact total number of units can be placed onto the syringe based on the addition of all injection points.

Figure 12A:
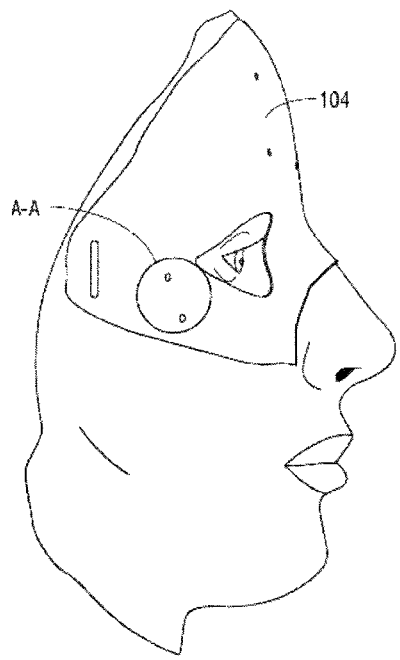
FIG. 12A is side perspective view of a mask in accordance with one embodiment of the present invention.
Figure 12B:
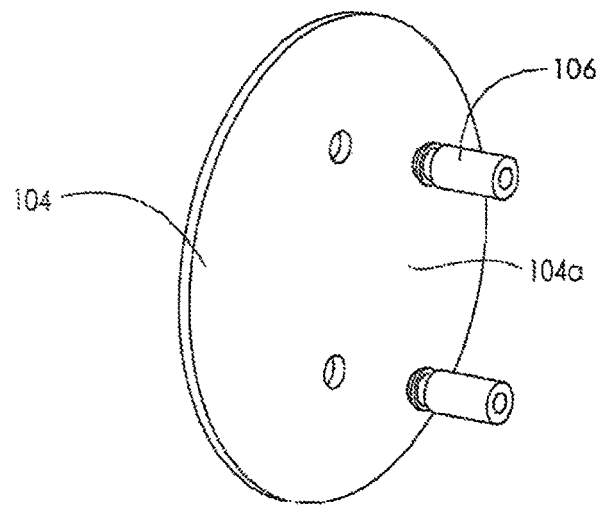
FIG. 12B is an enlarged view of the area of detail A-A identified in FIG. 12A showing the guide channels in accordance with one embodiment of the present invention prior to attachment to the mask.
Figure 12C:
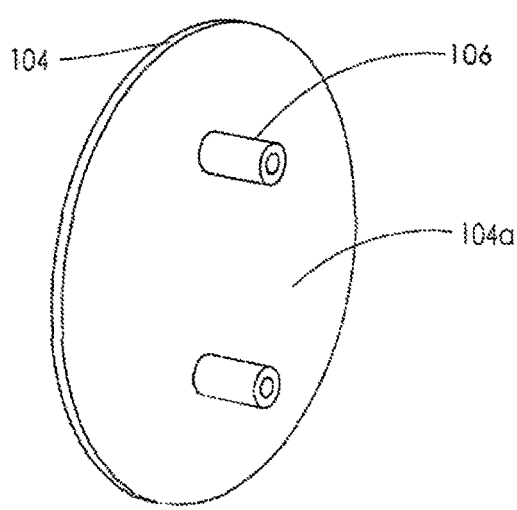
FIG. 12C is an enlarged view similar to FIG. 12B showing an alternate embodiment wherein the guide channels are built into (integral with) the mask.
Figure 12D:
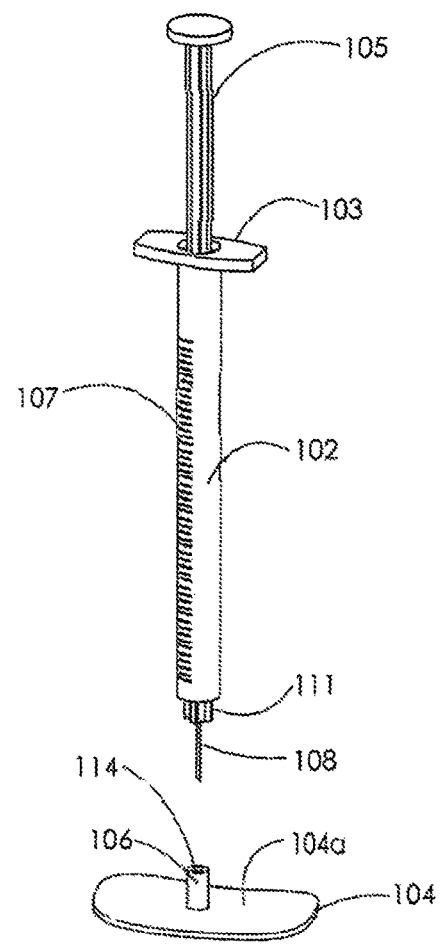
FIG. 12D is a perspective view showing a syringe (injection device) prior to insertion into the syringe guide channel (extending from a portion of the mask) of FIG. 12B.
Figure 13:
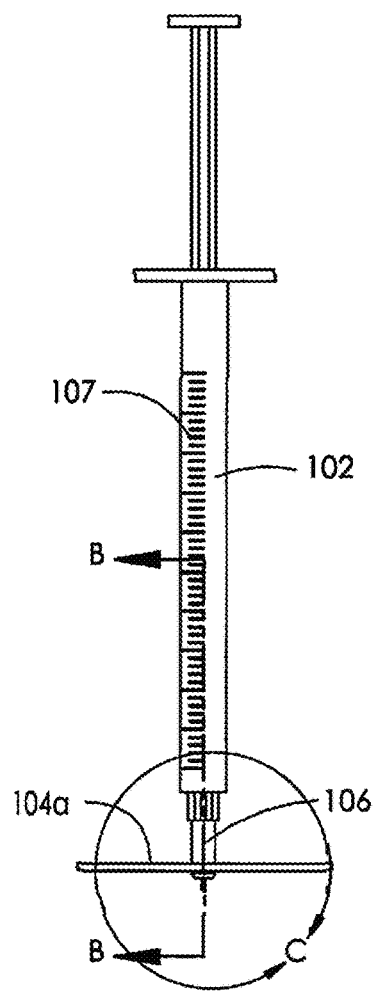
FIG. 13 is a front view showing the syringe inserted into the guide channel of FIG. 12B.
Figure 14:
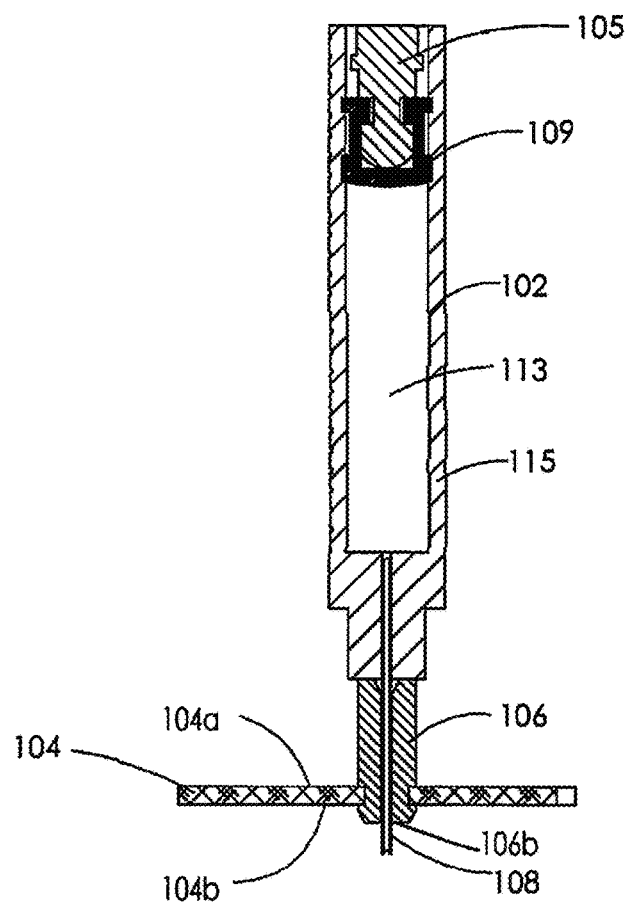
FIG. 14 is a cross-sectional view taken along line A-A of FIG. 13.

In the embodiment of FIG. 12D, the distal portion of the syringe 102 abuts the top of the guide channel 106. In the alternate embodiment of FIGS. 19-21, a wider guide channel is provided such that a distal portion of the syringe fits inside the guide channel. More specifically, guide channel 124 of FIGS. 19-21 extends upwardly (proximally) from the upper surface (proximal surface) of the mask 104, and can be integral with the mask 104 (as in FIG. 12C) or a separate component with a flexible feature inserted through the pre-formed hole in the mask (as in FIG. 12B). The guide channel 124 is identical to guide channel 106 except for its increased width, i.e., diameter. Syringe 120, having plunger 125, seal 127, barrel 123 and fluid chamber 129, is inserted through opening 126 and through the lumen of the channel guide 126 and through the hole 116 of the mask 104. The syringe 120 is inserted until the bottom wall 123a of barrel 123 contacts, i.e., abuts, the wall 124a within the lumen of guide channel 124. Thus, the distal portion of the barrel 123 is within the confines of wall 124b of channel guide 124. Wall 124a of guide channel 124 acts as a stop to limit the depth of insertion of the syringe and thus the depth of extension of the needle, to thereby control the depth of injection. Thus, with this wider channel guide design, the channel guide encapsulates the body of the syringe to guide the needle through. The depth of the needle is controlled by the design of the channel guide component and how far it lets the syringe be inserted. The height H3 of the wall can be of various heights to provide different depths of insertion. It is also contemplated that the guide channel itself can be provided with an adjustable wall to adjust the height of the individual guide channel to accommodate varying desired depths of insertion. Except for the foregoing, i.e., wider opening for receipt of the syringe therein, guide channel 124 is identical to guide channel 106 so the discussion of guide channel 106 of FIGS. 12A-18 and its functions are fully applicable to guide channel 124 of FIGS. 19-21.

In the embodiment of FIG. 12B, the guide channels are inserted into the pre-formed holes in the mask for securement thereto. In the alternate embodiment of FIG. 12C, the guide channels 106' are integral with the mask 104' and thus do not require separate insertion either in manufacture or by the user.

In alternate embodiments, the guide channel is provided on a flat support, and the support is attached to the mask. This differs from the foregoing embodiments wherein the guide channel is secured directly to the mask. FIGS. 22A-24 provide an example of such separate support which is secured to the mask by adhesive. Support 130 has a top surface 130a from which guide channel 132 extends proximally. On the bottom or distal surface 130b of the support 130, an adhesive material is attached. Thus, support 130 forms an adhesive pad which is secured to the mask 200 so that the opening 134 and lumen 134a within guide channel are aligned with the pre-formed hole in the mask. The syringe is the same as the syringe of FIG. 19 so has been labeled with the same reference numerals.

In use, the supports 130, with the exposed adhesive bottom surface, are adhesively secured to the mask so that the channel opening 133 is in alignment with the hole in the customized mask. The syringe 120 (with optional gradations 128) is inserted through the channel, until the distal portion bottoms out on the wall 132b (similar to wall 124a of guide 124 of FIG. 21). This provides a stop for syringe insertion to control the depth of needle penetration. When inserted through the channel, the needle 122 extends though the lumen 132a and distally beyond the support 130 into the body. Advancement of plunger 125 injects the fluid from the chamber 113 of the syringe 120. In some embodiments, the adhesive can be covered until ready for attachment wherein the cover can be peeled off to expose the adhesive surface.

The injection depth D3 is controlled by the height H3 of the channel guide component H3 and this height can be varied to achieve different injection depths. Alternatively, the needle height could be varied to achieve different injection depths. Another way to control the depth is to vary the thickness of the mask, with a thicker mask providing a shorter injection depth and a thinner mask providing a greater penetration depth.

Note the guide channel 130 could alternatively be configured so that the syringe remains outside the guide channel (rather than positioned therein) as in the embodiment of FIG. 15. Also, although adhesive is disclosed for attachment, other ways to attach the pad carrying guide channel are also contemplated.

In the alternate embodiment of FIGS. 35A-48, mini syringes are inserted into guide channels having a click-in or snap-in component. This click in syringe guide can be inserted into the mating feature of the mask before the syringe or together with the syringe.

Figure 35A:
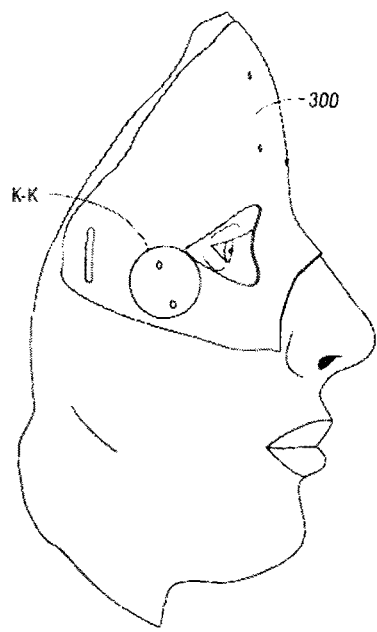
FIG. 35A is side perspective view of a mask (cover) in accordance with another alternate embodiment of the present invention.
Figure 35B:
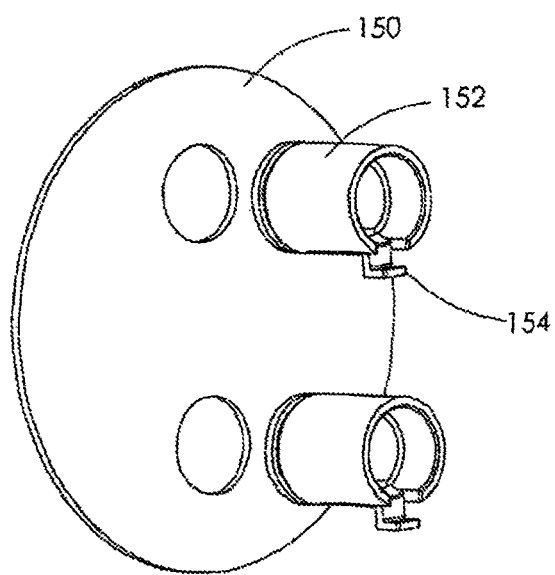
FIG. 35B is an enlarged view of the area of detail K-K identified in FIG. 35A showing the guide channel supports (mask mating features) in accordance with one embodiment of the present invention, the supports shown prior to attachment to the mask.
Figure 35C:
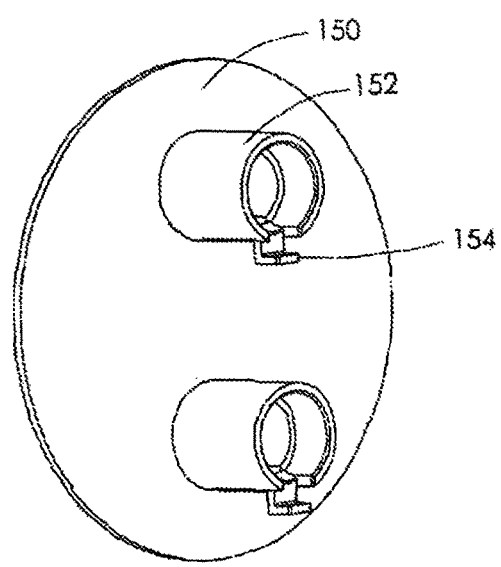
FIG. 35C is an enlarged view similar to FIG. 35B showing an alternate embodiment wherein the guide channel supports are built into (integral) with the mask.
Figure 35D:
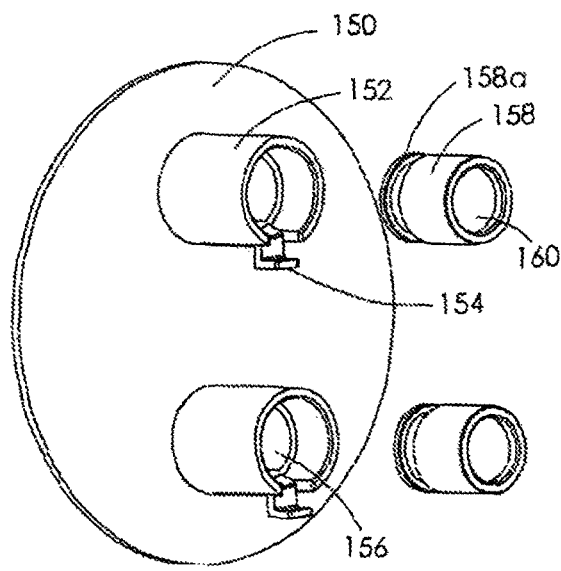
FIG. 35D is an enlarged view similar to FIG. 35B showing the syringe guide channels prior to insertion into the guide channel supports f FIG. 35B.
Figure 35E:
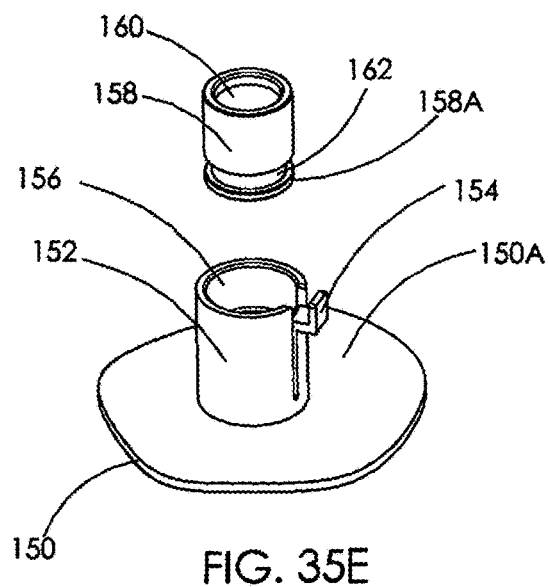
FIG. 35E is a perspective view of the support and the syringe guide channel of FIG. 35D prior to insertion of the guide channel into the support.
Figure 36:
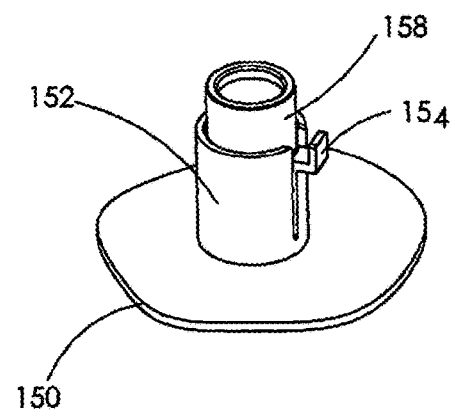
FIG. 36 is a perspective view showing the syringe guide channel of FIG. 35E inserted into the support of the mask.
Figure 37:
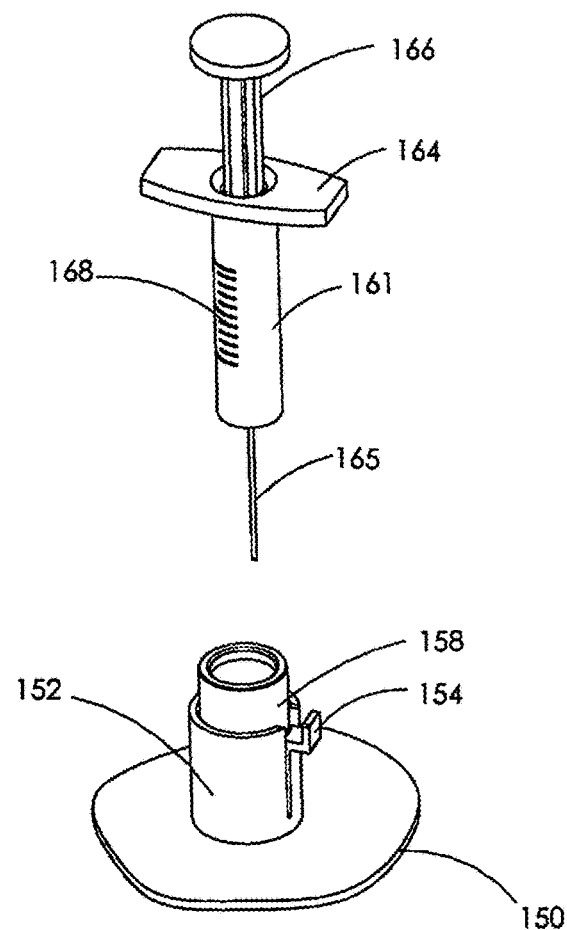
FIG. 37 is a perspective view showing the syringe prior to insertion into the guide channel of FIG. 36.
Figure 38:
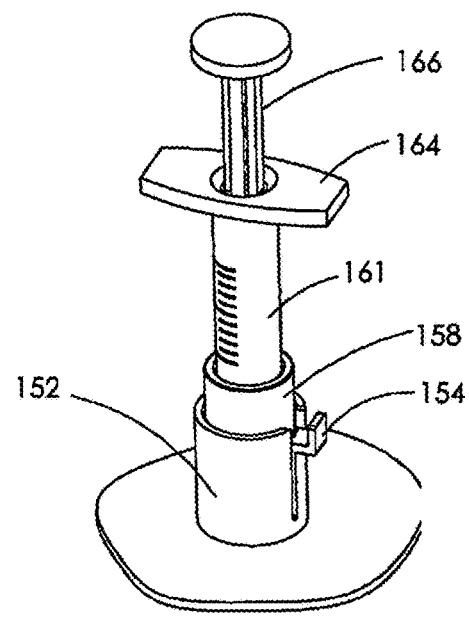
FIG. 38 is a perspective view showing the syringe inserted into the guide channel of FIG. 36.
Figure 39:
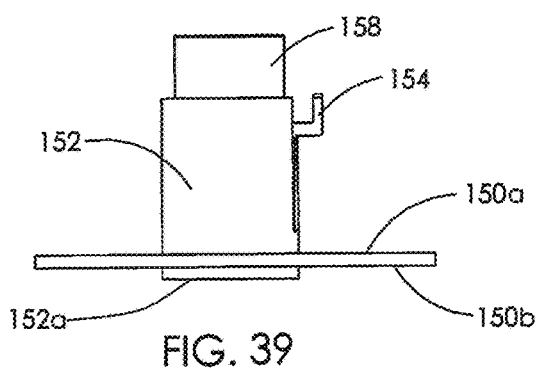
FIG. 39 is a side view showing the syringe guide channel of FIG. 35D clicked into the support (mating feature) of the mask.
Figure 40:
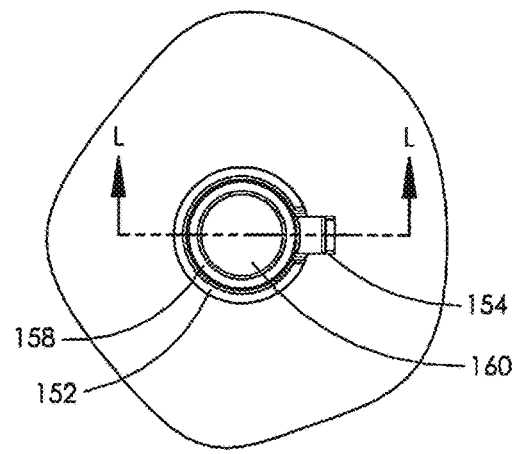
FIG. 40 is a top view of the syringe guide channel of FIG. 35D.
Figure 41:
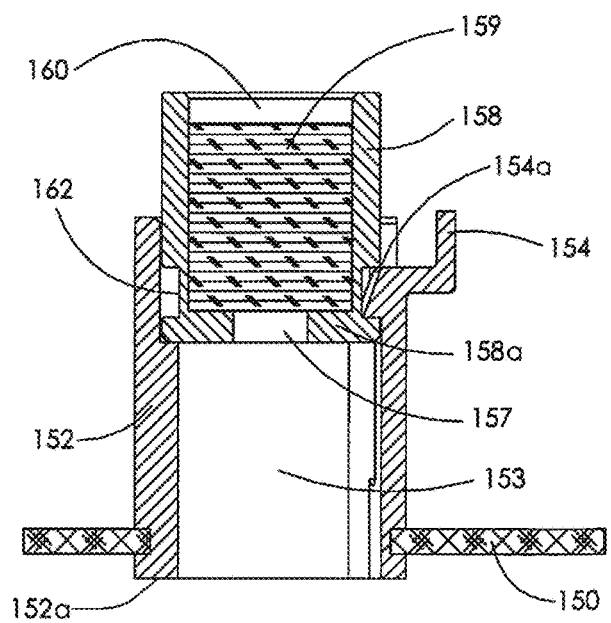
FIG. 41 is a cross-sectional view taken along line L-L of FIG. 40.
Figure 42:
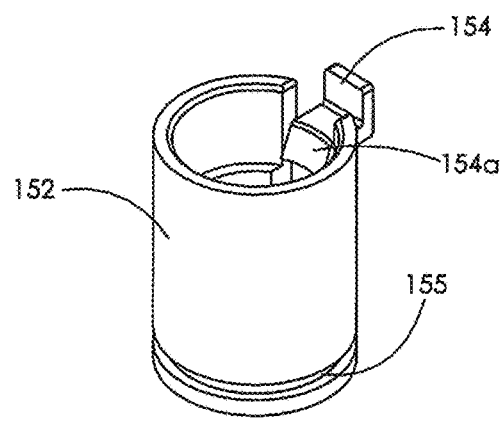
FIG. 42 is a perspective view of the support of FIG. 35D.
Figure 43:
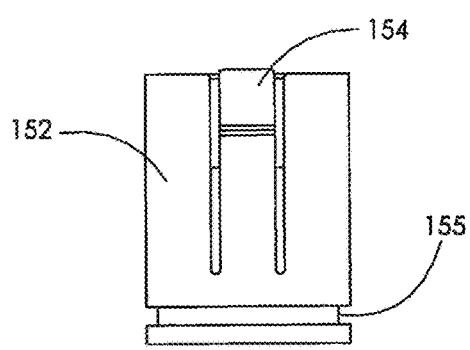
FIG. 43 is a side view of the support of FIG. 35D.
Figure 44:
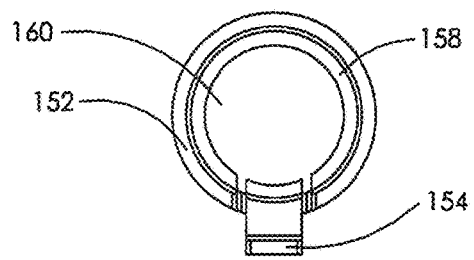
FIG. 44 is a top view of the support of FIG. 35D.

More specifically, the syringe guide channel 158 has an opening 160 communicating with the lumen to receive the syringe 160. The guide channel 158 is inserted into the mating feature 152, also referred to herein as the guide receiver. The receiver 152 can be integral with mask 150 as shown in FIG. 35C or a separate component attached to the mask as shown in FIG. 35B, which can be either removable or permanently (non-removably) attached. (Note the Figures illustrate a section of the mask in the same manner as detailed section 104a of the mask 104 of FIG. 12A and thus only two receiver/guide channels are shown in FIGS. 35A-35D and a single receiver and guide channel are shown in FIGS. 35E-38). If a separate component, the receiver 152 can include a flange and a recess for insertion through the pre-formed holes in the customized mask 150. Whether integral or separately attached component, receiver 152 extends proximally (outwardly) from upper (proximal) surface 150a of mask 150 and is dimensioned to receive the guide channel 158 within its lumen. Guide channel 158 is inserted through opening 156 in receiver 152 and into the lumen of the receiver, and protrudes proximally of receiver 152. The syringe guide 158 is clicked into the receiver 152 via the flexible tab 154 which is spring biased inwardly. When the guide channel 158 is inserted into receiver 152, it initially forces tab 154 outwardly as its outer wall engages the inner surface 154a of the tab 154 until the inner surface 154a is aligned with circumferential notch (recess) 162 of guide channel 158 as shown in FIG. 41. When so aligned, the tab 154 can return to its initial position to secure the guide channel 158 to the receiver 152. Thus, the flexible tab 154 of the mating component 152 allows the user to insert new syringe guides and remove them once they have been used. The syringe guide 158 can include a collapsible material 159, such as a sterile sponge, within its lumen as shown in FIG. 41.

Figure 45:
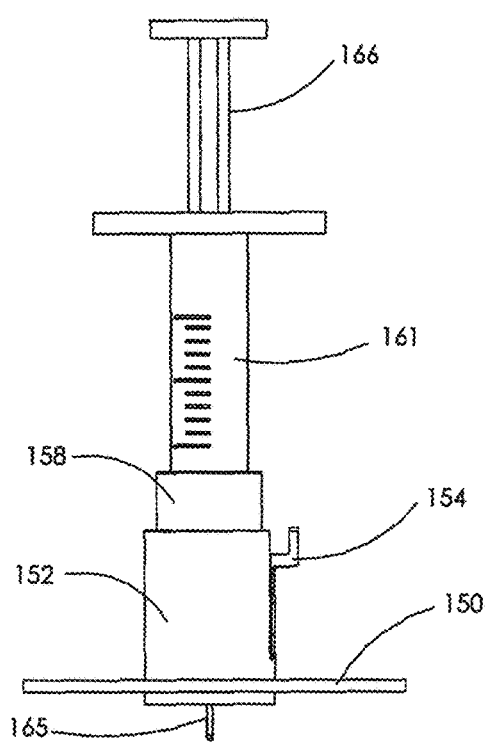
FIG. 45 is a side view of the syringe inserted into the guide channel of FIG. 36.
Figure 46:
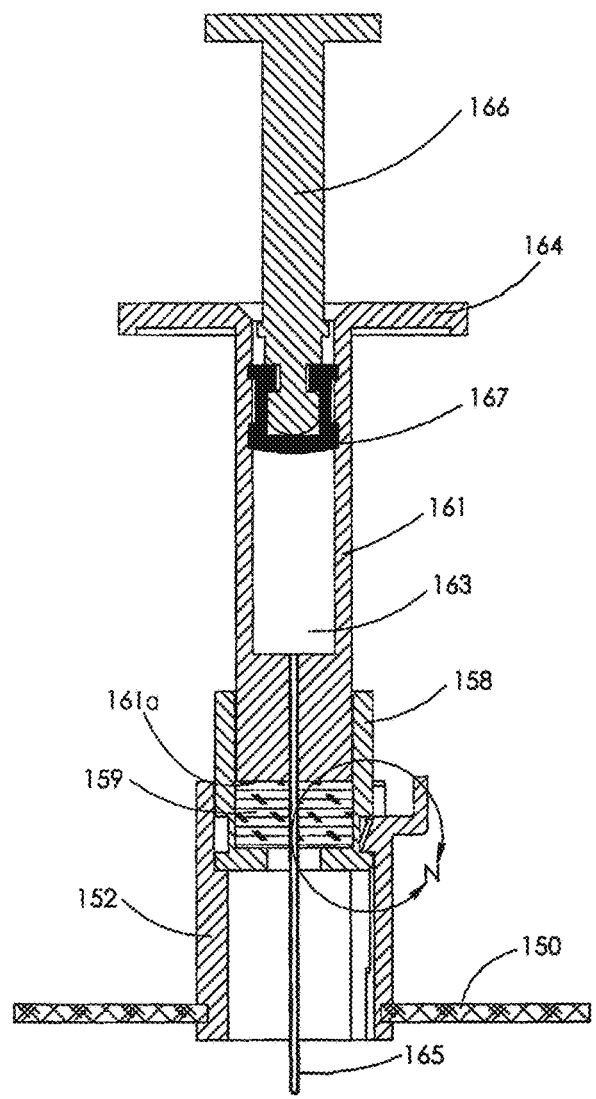
FIG. 46 is cross-sectional view showing the syringe inserted into the guide channel of FIG. 36.
Figure 47:
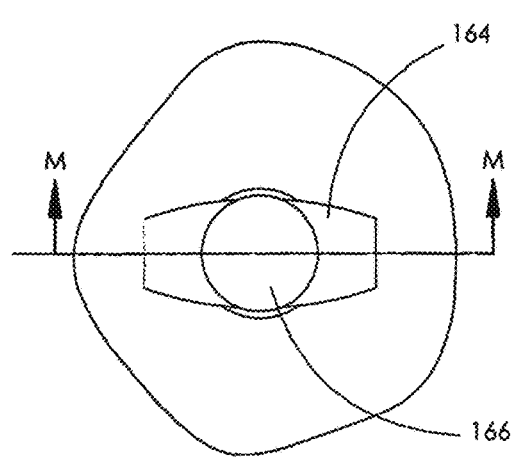
FIG. 47 is a top view of the syringe and guide channel of FIG. 45.
Figure 48:
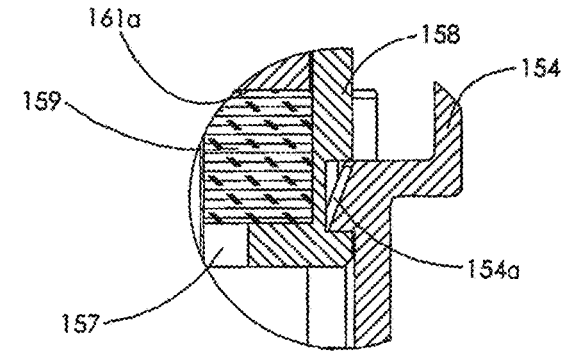
FIG. 48 is an enlarged view of the area of detail N of FIG. 46.

The syringe guide 158 aligns the syringe 161 to inject at the right location as can be appreciated in FIGS. 45 and 46. As the user presses the syringe collar down when the syringe 161 is inserted into the guide 158, the collapsible material 159 will compress (due to distal wall 161a) allowing the needle 165 to enter the tissue as it extends through the opening 157 in wall 158a of syringe guide 158 and through lumen 153 of receiver 152 and past the distal surface of mask 150. The user then holds handle (flange) 164 and presses the plunger 166 to inject the medication from the chamber 163 within the syringe 161. The collapsible material 159 allows the user to safely align multiple syringes without the needle contacting the skin and can spring back up following the injection. A seal 167 similar to seal 127 of FIG. 21 can be provided within the barrel of the syringe 161.

As noted above, the customized masks (covers) of the present invention are not limited to covering the face or forehead of the patient but can be applied to other parts of the body. FIGS. 25-34 illustrate such alternative by way of example, showing a cover (mask) placed over an abdominal section of the patient, which is contoured around a shape to align with the patient's body. The customized "abdominal mask" (cover) 140 includes pre-formed openings for injection locations and is made in accordance with the processes described herein. The mask 140 can be used for example for abdominal fat dissolving/destruction. Cover 140 has a plurality of guide channels 144 which can be integral with the cover 140, i.e., built directly into the cover 140, as shown, or, alternatively, separately attached to the cover in the same ways as discussed above with respect to the other embodiments. These guide channels 144 are aligned with the openings in the customized mask 140 to provide passage of the syringes. The guide channels 144 can control the depth of the injections. For example, in FIG. 33, a taller guide channel (H4) yields a shallower injection (D4) while in FIG. 34 a shorter guide channel (H5) yields a deeper injection (D5). The mask 140 can be provided with different height channel guides to regulate different injection depths at different sites, or the needle lengths can be varied to achieve different injection depths or the thickness of the mask can vary.

Figure 27:
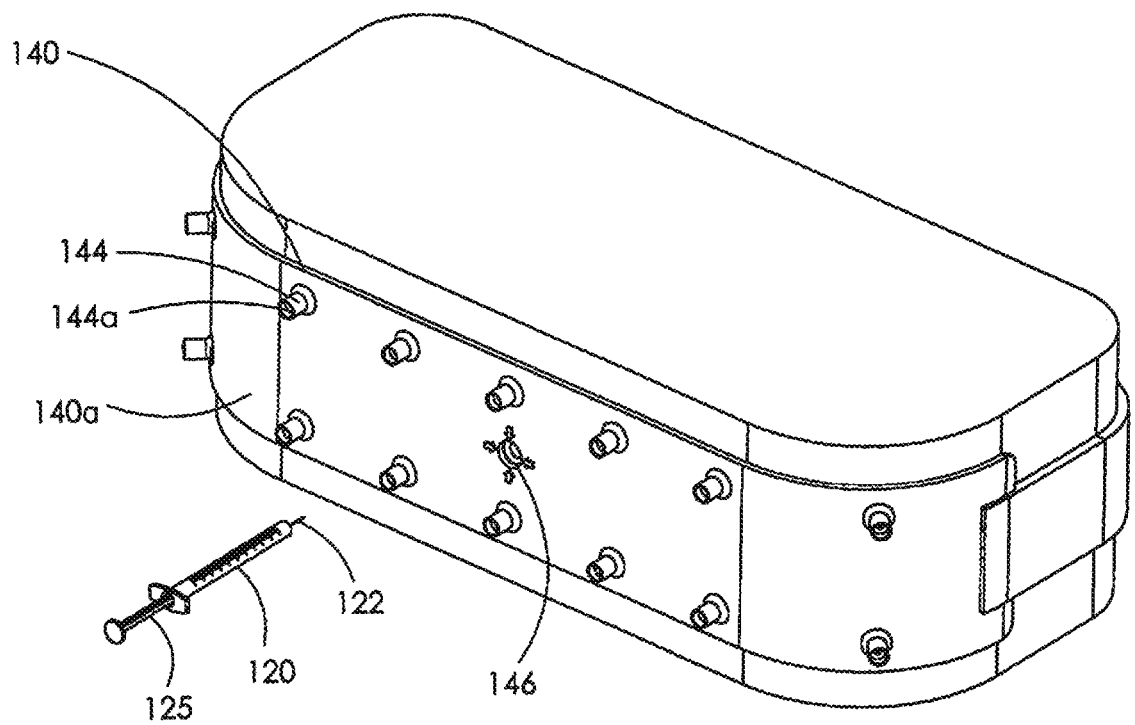
FIG. 27 is a view similar to FIG. 25 showing the syringe prior to insertion into the guide channel of the abdominal mask.
Figure 31:
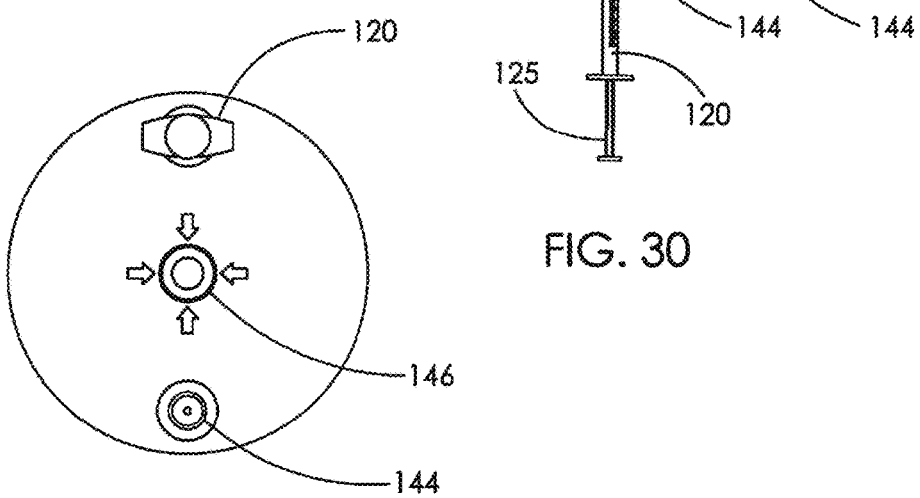
FIG. 31 is a close up view of the area of detail H of FIG. 29 showing the guide channel and umbilicus alignment hole of the mask of FIG. 25, and further showing a syringe inserted into one of the guide channels.

The cover 140 has distal and proximal surfaces 140a, 140b and includes an umbilical alignment hole 146 with arrows to ensure the user aligns the cover 140 correctly. FIGS. 27 and 31 show the alignment hole 146 for the umbilicus.

Strap 142 extends from the edge of the cover 140 and wraps around the abdomen, and is secured at region 143 by Velcro, although other ways to secure the cover 140 or strap 142 are also contemplated such as clips, hooks, clasps, etc. The strap 142 tightens the cover 140 to the body.

Figure 28:
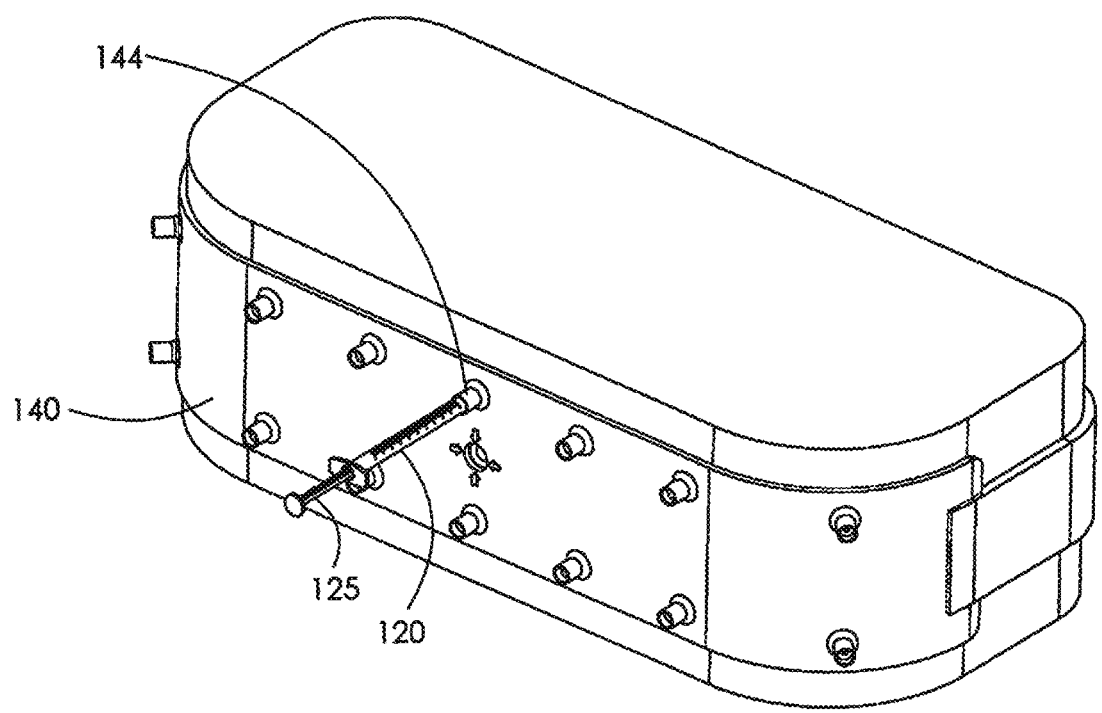
FIG. 28 is a view similar to FIG. 27 showing the syringe inserted into the guide channel of the abdominal mask.
Figure 29:
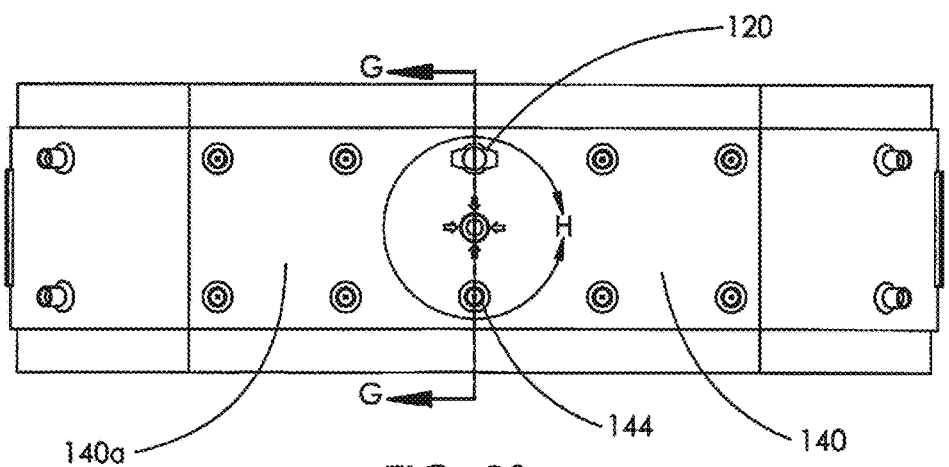
FIG. 29 is a front view of an abdominal mask of FIG. 25.
Figure 30:
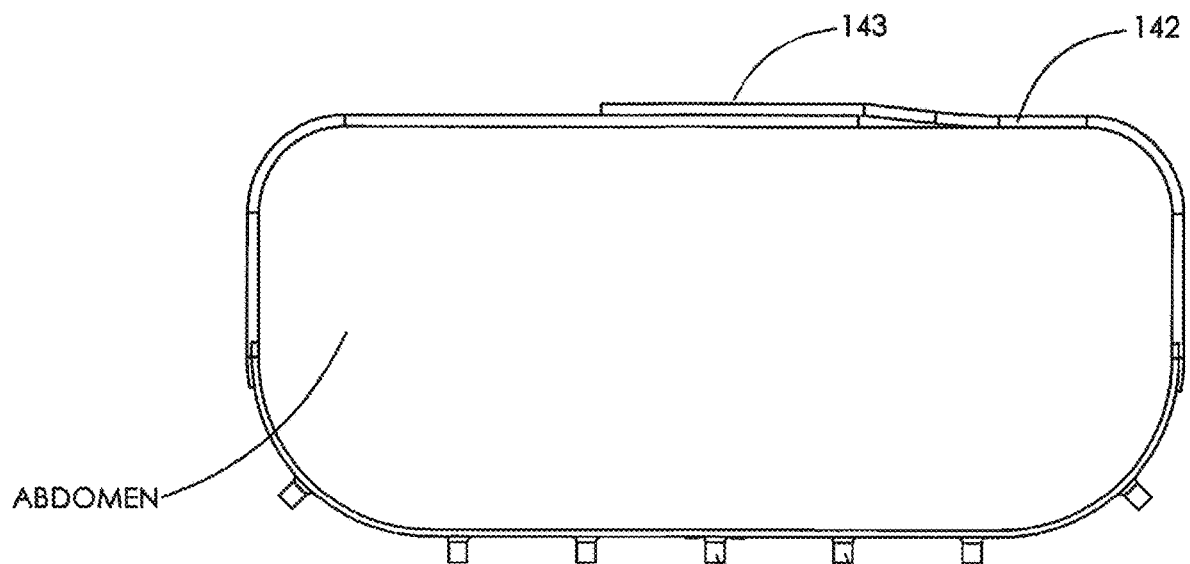
FIG. 30 is a top view of the abdominal mask of FIG. 25.

In use, the syringes 120 are inserted into the guide channels 144 as shown in FIGS. 28 and 32 so that the needle 122 extends through the opening 144a and lumen 144b of guide 144. Syringe 120 bottoms out at wall 144c so that the wall 144c of guide 144 provides stop to limit the depth of insertion of the syringe 120 and thus the depth of penetration of the needle 122 and injection of the fluid. Once the syringes are inserted, the plunger 125 is depressed to inject the fluid from chamber 129 of the syringe.

In the embodiments disclosed herein, the channel guides can be made from silicone or rubber of varying durometer to safely ensure the passage of the needle without damaging the needle. The guide channels are preferably designed with a slight lead-in around the needle guide hole, preferably minimal, to reduce the likelihood of the user hitting the mask with the needle and bending or breaking the needle.

In alternate embodiments, the syringe alignment features can be dimensioned to be much taller than the needle, in which case the entire body of the syringe will be aligned before the needle even gets to the surface of the needle guide hole/mask.

Figure 9:
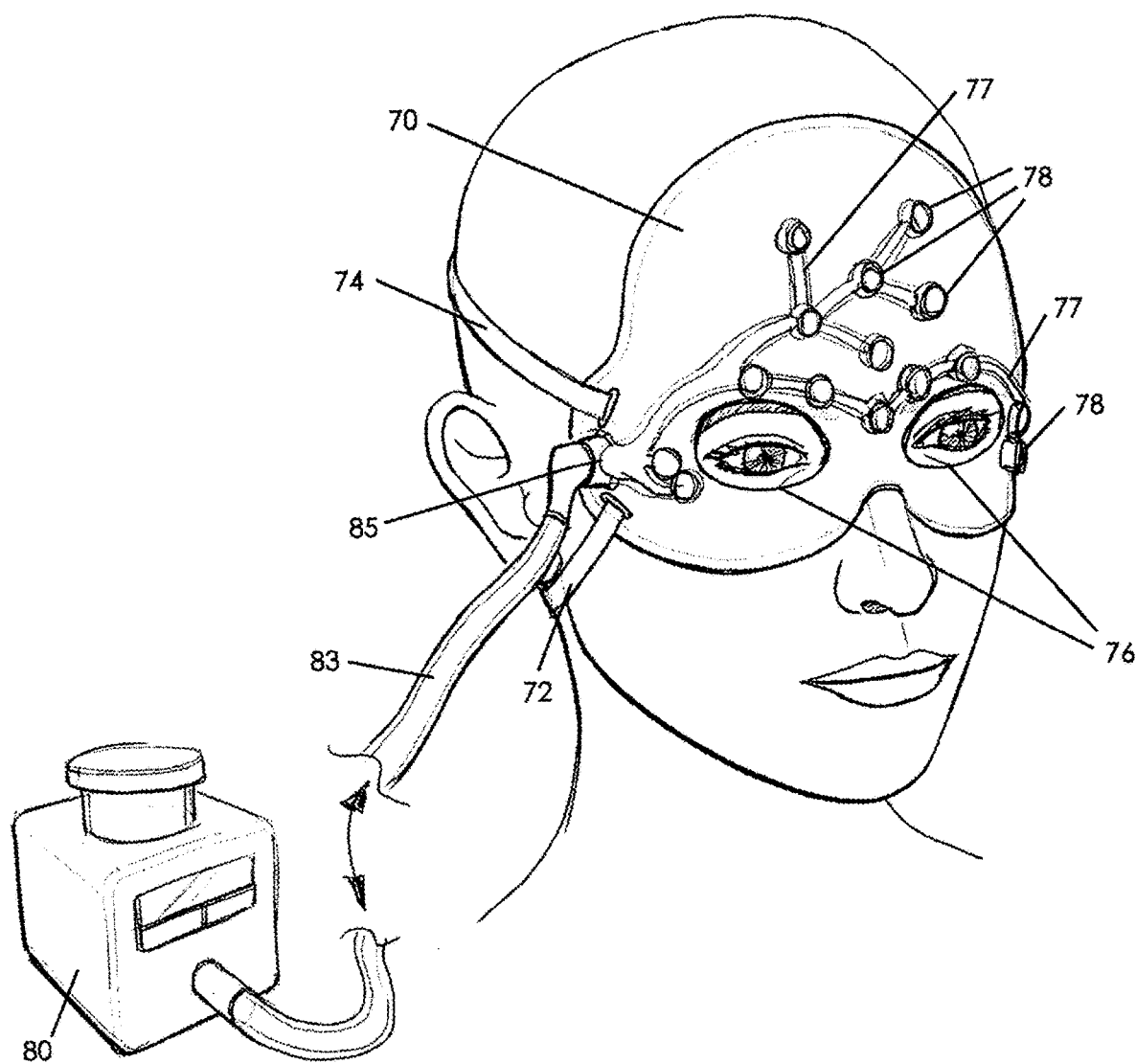
FIG. 9 is a front perspective view of another alternate embodiment of a customized forehead and lateral eye mask of the present invention having an external injection mechanism.

In the embodiment of FIG. 9, a built in pneumatic mechanism or other mechanism is utilized to deliver the fluid from the syringes at the same time. Mask 70 has a series of holes 78 which receive injection devices and are connected via channels 77 to external fluid injection control device 80. Only some of the holes 78 and channels 77 are labeled for clarity. Tube 83 extends from control device 80 and is in fluid communication with channels 77 of mask 70 so that air (or other powering fluid) can be delivered through the channels 77 and into the injection devices mounted to the holes 78. In this manner, instead of actuating each syringe by individually injecting each syringe by pushing with the finger, the control device 80 provides a system to simultaneously actuate the syringes. The tube mount 85 in the illustrated embodiments is at the side of the mask, but could, in alternate embodiments, be provided in other regions of the mask, to provide fluid communication with the syringes mounted at the holes in the mask to effect injection. The mask 80 is in the form of mask 10 with straps 72, 74 and eye slits (openings) 76, although this "force" mechanism can be used with the other masks disclosed herein. The control unit 80 can be a pneumatic system or other mechanism for delivering a force to force the toxin from the syringes transdermally through the respective hole. The injection devices, e.g., syringes, can be preloaded syringes or replaceable syringes as in the foregoing embodiments. The arrangement and communication of the interconnected channels 78 of FIG. 9 is just one example as the channels can be arranged and communicate in other arrangements. The mask 70 is in the form of mask 10 with straps 72, 74 and eye slits (openings) 76. It should be appreciated that the system of FIG. 9 with the built in channels is shown by way of example as it can be provided on mask 20 or other masks disclosed herein. Note in an alternate embodiment, the injection control device 80 can, in addition to containing the pump or other force mechanism, also contain the fluid, e.g., toxin, or, alternatively contain the force mechanism and be provided with another tube connected to the toxin source, and the channels, holes and/or syringes could be configured to control the dosage.

As can be appreciated, the system and methods/processes of the present invention address three variables: a) the customized mask controls injection location; b) the injection device controls the amount of fluid injected; and c) the mask configuration (or alternatively the injection device configuration) controls the depth of the injection.

The customized masks of the present invention can be provided with identification such as the name of the patient. Additionally, the customized masks can have pre-printed dosages (units) next to each guide hole to facilitate injection. The dosages can be based on the patient's answers to the questions used to assemble the data and create the mask, or alternatively provided by the physician/practitioner. These reusable masks would then be shipped to the physician's office or alternatively shipped to the patent and brought by the patient to the physician's office as described above. The pre-printed information on the mask can then be used to guide the injections. This advantageously reduces the variability in injection location as well as dosage.

As described above, the customized masks of the present invention could alternatively come with pre-filled small syringes built into the mask with reconstituted botulinum toxin. The dosage would be based on questions the patient answers. This custom mask could be shipped directly to a physician office or patient. This could expand the access of patients to these injections as any practitioner could apply the mask and push the buttons to inject with reproducible accuracy.

In some embodiments, kits of pre-loaded syringes of medication can be shipped to the physician office or shipped directly to the patient for home administration. The syringes can be disposable or reusable by being re-Tillable. In some embodiments, kits containing the mask and injection devices (either pre-filled or empty shipped with the fluid separate) can be shipped to the physician office or patient.

The customized masks not only allow predictability but the masks in some embodiments can be re-used so repeated treatment can be ensured to be in the same locations. Also, the shipments of medication to the physician or patient for use with the re-used mask can vary depending on the results of prior injections.

In the foregoing embodiments, the physician or healthcare provider. e.g., nurse, physician assistant, pharmacist, performs the injection, however, it is also contemplated in alternate embodiments that the patient can perform the injection. Thus, in these embodiments, the botulinum toxin is self-injected/self-administered by the patient. Thus, for example, instead of the step of injections by the physician in the process of FIGS. 2A and 2B, the step of injection would be performed by the patient. Pre-loaded syringes would facilitate patient injection.

In an alternate embodiment, instead of a 3D scanner, the physician takes 2D photos in the office and makes the recommended markings on the photos based on the physician's knowledge about the patient and the patient's previous injections. The photos are then sent to another entity to do the 3D modeling and print the mask, which is then sent back to the physician or directly to the patient.

As noted above in the foregoing embodiments, the customized masks are created via 3D printing, however, it is also contemplated that other methods processes can be utilized to create the 3D masks.

In the foregoing embodiments, 3D customized masks for the patient are printed. In an alternate embodiment, instead of utilizing such 3D customized masks, for simplification, various size mask templates can be created. Thus, various size mask templates can be made, not 3D fitted to individual faces, but close fits to forehead/face size. These templates could then be given to physicians or patients and then brought to physician offices where a physician/practitioner could mark them, i.e., punch holes, to individualize them based on where the patient should or usually gets injections. This could then be used as a template on its own or it could be used to make a more permanent template with or without the syringes built into it. Thus, such masks would provide a customizable facial/head template to guide injections of the botulinum toxin.

Color coding, number/symbol coding or other forms of identification/designation of marked locations can be inputted prior to creation of the mask to inform the clinician of the number of units (dosage) to be injected. Such dosage indicators can be embossed or otherwise imprinted on the masks during creation so the printing of the mask includes the dosage indicators or alternatively the dosage indicators can be applied as stickers to the mask after it is formed. For example, different colors can be printed on the clear mask or decals can be applied to the mask by the technician/clinician.

Figure 10:
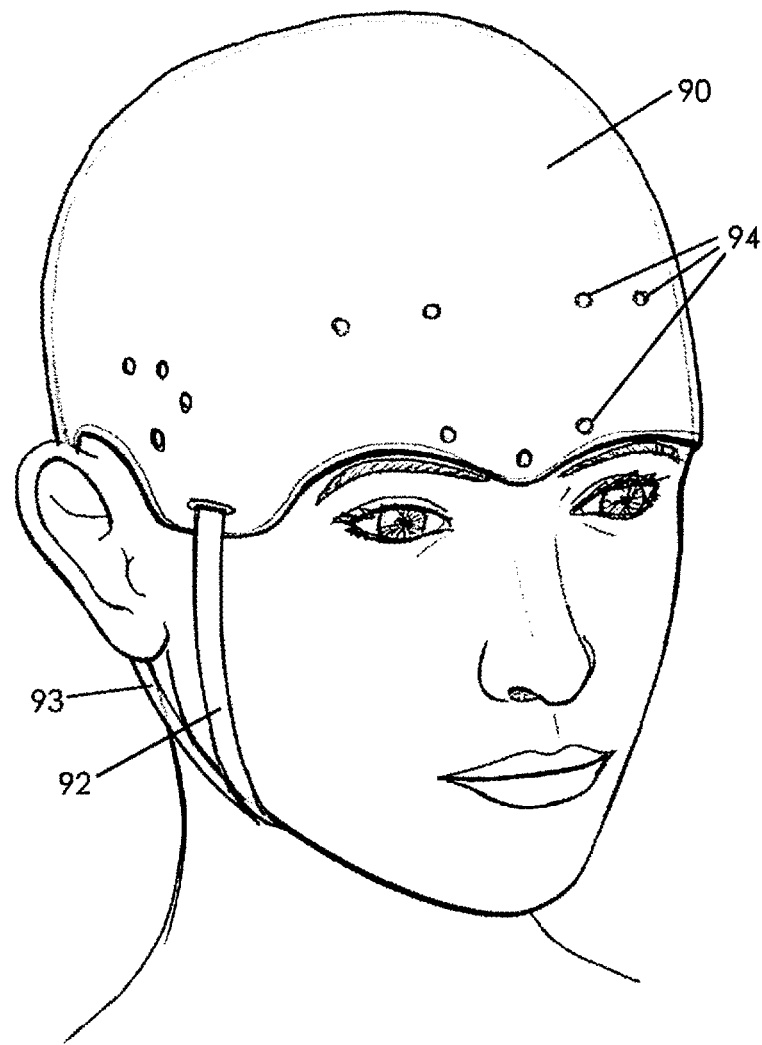
FIG. 10 is a front perspective view of another alternate embodiment of a customized mask of the present invention positioned on a patient's forehead and scalp.
Figure 11:
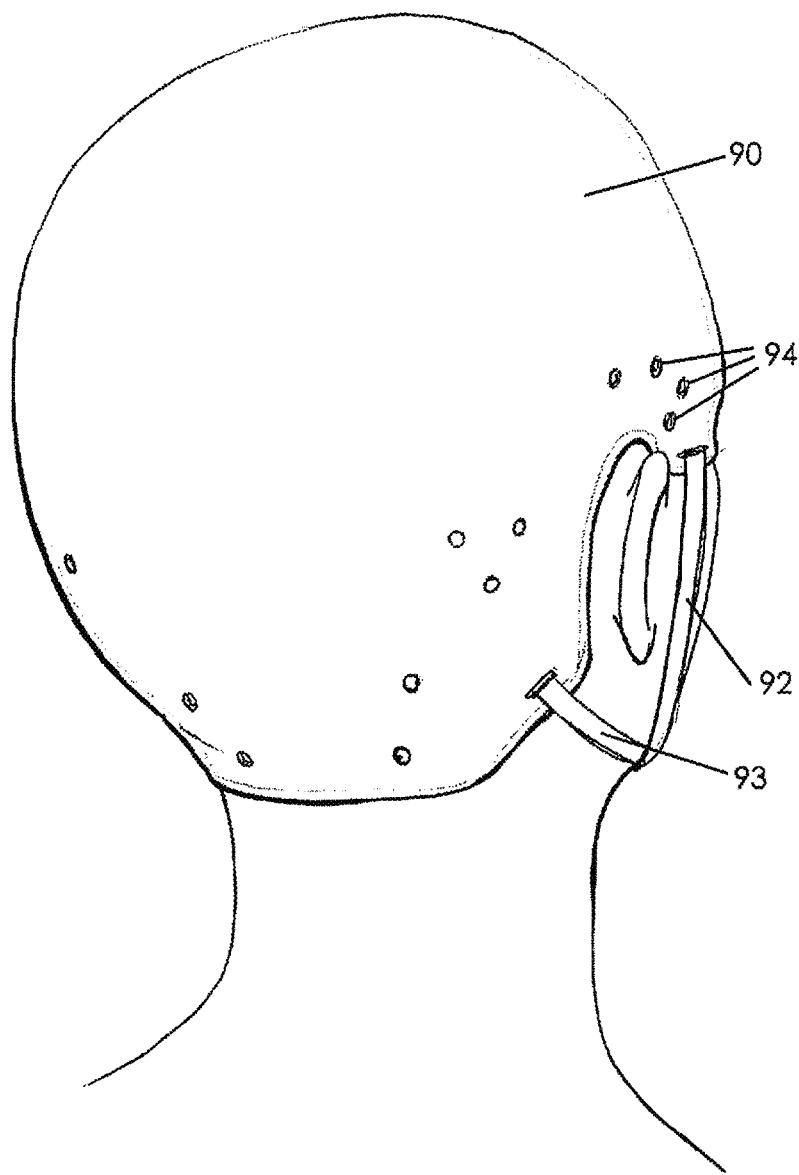
FIG. 11 is a rear perspective view of the customized mask of FIG. 10.

The present invention as described above in the various embodiments is used for injection of botulinum toxin for cosmetic surgery. However, the concepts/systems of any of the embodiments disclosed herein can also be used for other procedures. The masks can be created in the same way as in the systems/processes disclosed herein (or other ways, e.g., templates), except the masks can be created for placement on other regions such as for example the scalp and forehead. FIGS. 10 and 11 show by way of example a mask which extends over the scalp and can be used for treatment of migraines. More specifically, mask 90 covers the patient's scalp and has chin straps 92, 93 to secure the mask 90 and a series of holes 94 for fluid injection. The injections can be made via injection devices as described above, including, for example, the replaceable syringes as in FIG. 7, the pre-loaded syringes as in FIG. 8 or the channel system of FIG. 9. The present invention also contemplates use of botulinum toxin for other parts of the body, e.g., underarms for sweating.

It should be appreciated that different botulinum toxins can be injected. Botulinum toxin is the product of *Clostridium botulinum*. This growing bacteria produces the neurotoxin botulinum toxin, which inhibits the release of acetylcholine and results in the flaccid paralysis of the affected muscles. There are several distinct types of botulinum toxin: A, B, C1, D, E, F, and G. The various types of botulinum toxin are marketed under brand names such as Botox (onabotulinumtoxinA, Allergan) and Dysport/Azzalure (abobotulinumtoxinA, Ipsen/Galderma), Xeomin/Bocouture (incobotulinumtoxinA, Merz) and Jeuveau (prabotulinumtoxinA, Evolus/Daewoong), along with several others in clinical trials. Revance Therapeutics, Inc. also offers the neuromodulator DaxibotulinumtoxinA for Injection (RT002)

Although botulinum toxin is described as the fluid injected through the masks of the foregoing embodiments, it is also contemplated that other fluids can be utilized for other treatments or surgical procedures. For example, Kybella (deoxycholic acid), which is used to reduce fat, can be used on multiple surface areas of the body to target stubborn fat areas after a 3D printout of the mask is made.

It should be appreciated that the various imaging methods and the various ways to manufacture the masks disclosed herein are applicable to the masks of the present invention in which injection needles are provided through openings in the mask as well as applicable to the alternative masks of the present invention in which markings are made through the mask and the mask is removed for drug injection.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method for providing consistent injection of a drug through a skin of a patient, the method comprising the steps of:
   a) manually providing first markings on a skin of a patient to provide locators for drug injection, the first markings customized to anatomy of the patient and needs of the patient;
   b) taking a first image of the skin with the first markings thereon;
   c) storing the first image;
   d) prior to creation of a three dimensional customized cover, injecting the drug into the patient at the location of the first markings;
   e) after a period of time wherein the drug injected in step (d) has had time to work, and prior to creation of the cover, evaluating a result of the injection of the drug and by a physician editing an unsatisfactory first image to create a revised image to adjust one or more injection locations for injection at a location different than the first markings, wherein the revised image corrects the first markings of the unsatisfactory first image, the customized cover not made until the drug injected has time to work so the cover is thereby not made until the result is satisfactory;
   f) after obtaining the cover made in accordance with the revised image, placing the cover on the skin of the patient and manually providing second markings through openings in the cover, the openings formed in the cover customized for the individual patient and formed in response to instructions based on individual patient evaluation of step (e); and g) removing the cover and injecting the drug at the second markings, wherein the physician has direct visualization of the skin of the patient as injections are made.

2. The method of claim 1, further comprising marking the skin with varied color markings to indicate a different dosage of the drug for injection.

3. The method of claim 2, wherein the cover has designations integrally formed thereon to indicate dosage, and the method further comprises removing the cover and injecting the drug into the skin in accordance with the indicated dosage.

4. The method of claim 2, wherein the cover has designations applied to the cover after the cover is formed, and the method further comprises injecting the drug into the skin in accordance with the indicated dosage.

5. The method of claim 1, wherein the step of placing the cover comprises aligning the cover on the skin in accordance with one or more alignment markers on the cover.

6. The method of claim 1, further comprising uploading either the revised or not edited first image to a web portal for linking with a device for manufacturing the cover, wherein the web portal is configured to block access to software linked to the web portal.

7. The method of claim 1, wherein the cover includes dosage indicators thereon.

8. The method of claim 1, wherein the not edited first image or revised image is inputted to a website portal linked to a software application on a device which receives and processes data corresponding to desired locations of drug injection by the patient, based on the manually marked locations, to provide instructions for manufacture of the cover.

9. The method of claim 1, wherein the cover is formed by 3D printing.

10. The method of claim 1, wherein after uploading the first image to a web portal, the first image is manipulated in accordance with step (e) to provide instructions for manufacture of the cover.

11. The method of claim 1, wherein the cover is configured to prevent passage of injection devices through the openings.

12. The method of claim 1, wherein the cover is manufactured based on human editing on a software based application.

13. The method of claim 1, wherein the cover is made at a remote site and sent to the patient.

14. The method of claim 1, wherein the cover is made at a remote site and sent to a physician.

15. The method of claim 1, wherein the period of time exceeds one week.

16. The method of claim 1, wherein the cover is reusable on the patient and the method includes placing the cover on the skin and manually making markings on the skin through the openings multiple times for follow up injections with the cover removed.

17. The method of claim 1, wherein the first image is edited on a screen displaying the stored first image.

18. The method of claim 1, wherein a software application enables editing of the first image.

19. The method of claim 1, wherein the cover is customized based on a set of instructions provided from a software based application processing the revised image or first image if not revised.

20. The method of claim 1, wherein the openings in the cover accommodate markers for marking the skin but are configured to not accommodate injection devices.

21. The method of claim 6, wherein access is allowed only to the images.

* * * * *